United States Patent
Muraoka et al.

(10) Patent No.: US 10,849,886 B2
(45) Date of Patent: *Dec. 1, 2020

(54) COMBINATION THERAPY USING AZABICYCLO COMPOUND FOR CANCER

(71) Applicant: TAIHO PHARMACEUTICAL CO., LTD., Chiyoda-ku (JP)

(72) Inventors: Hiromi Muraoka, Tsukuba (JP); Akira Kanoh, Tsukuba (JP)

(73) Assignee: TAIHO PHARMACEUTICAL CO., LTD., Chiyoda-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/493,479

(22) Filed: Apr. 21, 2017

(65) Prior Publication Data

US 2017/0216261 A1 Aug. 3, 2017

Related U.S. Application Data

(63) Continuation of application No. 15/025,797, filed as application No. PCT/JP2014/075846 on Sep. 29, 2014, now Pat. No. 9,694,001.

(30) Foreign Application Priority Data

Sep. 30, 2013 (JP) ................................. 2013-205500

(51) Int. Cl.
| | |
|---|---|
| *A61K 31/437* | (2006.01) |
| *A61K 33/24* | (2019.01) |
| *A61K 45/06* | (2006.01) |
| *A61K 31/337* | (2006.01) |
| *A61K 31/454* | (2006.01) |
| *A61K 31/506* | (2006.01) |
| *A61K 31/517* | (2006.01) |
| *A61K 31/519* | (2006.01) |
| *A61K 31/5377* | (2006.01) |
| *A61K 31/704* | (2006.01) |
| *A61K 31/7048* | (2006.01) |
| *A61K 31/7068* | (2006.01) |
| *A61K 31/555* | (2006.01) |

(52) U.S. Cl.
CPC .......... *A61K 31/437* (2013.01); *A61K 31/337* (2013.01); *A61K 31/454* (2013.01); *A61K 31/506* (2013.01); *A61K 31/517* (2013.01); *A61K 31/519* (2013.01); *A61K 31/5377* (2013.01); *A61K 31/555* (2013.01); *A61K 31/704* (2013.01); *A61K 31/7048* (2013.01); *A61K 31/7068* (2013.01); *A61K 33/24* (2013.01); *A61K 45/06* (2013.01)

(58) Field of Classification Search
CPC ... A61K 31/437; A61K 31/337; A61K 31/454
See application file for complete search history.

(56) References Cited

U.S. PATENT DOCUMENTS

| | | | |
|---|---|---|---|
| 9,694,001 B2* | 7/2017 | Muraoka | A61K 45/06 |
| 2007/0123546 A1 | 5/2007 | Machajewski et al. | |
| 2009/0247524 A1 | 10/2009 | Tsukuda et al. | |
| 2009/0297473 A1 | 12/2009 | Maier et al. | |
| 2010/0004237 A1 | 1/2010 | Machakewski et al. | |
| 2010/0056510 A1 | 3/2010 | Shimma et al. | |
| 2012/0108589 A1* | 5/2012 | Kitade | C07D 209/08 |
| | | | 514/234.2 |

FOREIGN PATENT DOCUMENTS

| | | |
|---|---|---|
| EP | 2 452 940 A1 | 5/2012 |
| JP | 2004-512381 A | 4/2004 |
| WO | WO 2006/066937 A2 | 6/2006 |
| WO | 2007/039403 A1 | 4/2007 |
| WO | 2007/041362 A1 | 4/2007 |
| WO | 2007/138994 A1 | 12/2007 |
| WO | 2008/105526 A1 | 9/2008 |
| WO | 2011/004610 A1 | 1/2011 |

OTHER PUBLICATIONS

National Cancer Institute; Docetaxel, Oct. 5, 2006.*
Office Action dated Jun. 20, 2017 in Russian Patent Application No. 2016116777 (with English language translation).
D.A. Kharkevich, "Pharmacology: Text book.—9th edition, revised and supplemented," M.:Geotar-Media, 2006, pp. 66-67.
Zev A. Wainberg, et al. "Inhibition of HSP90 with AUY922 induces Synergy in HER2-Amplified Trastuzumab-Resistant Breast and Gastric Cancer," Molecular Cancer Therapeutics, Apr. 2013; 12 (4), pp. 509-519.
International Search Report dated Dec. 16, 2014 in PCT/JP2014/075846 filed on Sep. 29, 2014.
Luke Whitesell, et al., "HSP90 and The Chaperoning of Cancer", Nature Reviews, vol. 5, Oct. 2005, pp. 761-772.

(Continued)

*Primary Examiner* — Pancham Bakshi
(74) *Attorney, Agent, or Firm* — Oblon, McClelland, Maier & Neustadt, L.L.P.

(57) ABSTRACT

Provided is a novel method for treating cancer using an HSP90 inhibitor which exhibits a markedly superior antitumor effect and has a reduced side effect.
An antitumor agent is characterized in that an azabicyclo compound of the following Formula (1) or a salt thereof is administered in combination with other antitumor agent(s).

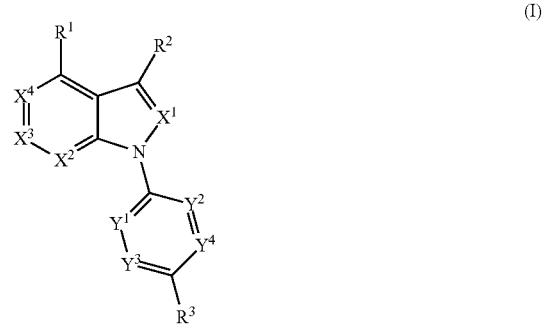

(I)

11 Claims, 4 Drawing Sheets

(56) References Cited

OTHER PUBLICATIONS

Adeela Kamal, et al., "Therapeutic and diagnostic implications of Hsp90 activation", Trends in Molecular Medicine, vol. 10, No. 6, Jun. 2004, pp. 283-290.

Udai Banerji, "Heat Shock Protein 90 as a Drug Target: Some Like It Hot", Molecular Pathways, Clin Cancer Res, vol. 15, No. 1, Jan. 2009, pp. 9-14.

Tony Taldone, et al. "Targeting Hsp90: small-molecule inhibitors and their clinical development", Current Opinion in Pharmacology, vol. 8, 2008, pp. 370-374.

Yanyan Li, et al. "New developments in Hsp90 inhibitors as anti-cancer therapeutics: Mechanisms, clinical perspective and more potential", Drug Resistance Updates, vol. 12, 2009, pp. 17-27.

David A. Proia, et al., "Synergistic activity of the Hsp90 inhibitor ganetespib with taxanes in non-small cell lung cancer models", Preclinical Studies, Invest New Drugs, vol. 30, No. 6, 2012, pp. 2201-2209.

Xiangyi Lu, et al., "Hsp90 inhibitors and drug resistance in cancer: The potential benefits of combination therapies of Hsp90 inhibitors and other anti-cancer drugs", Biochemical Pharmacology, vol. 83, No. 8, 2012, pp. 995-1004.

Extended European Search Report dated Jan. 31, 2017 in Patent Application No. 14849447.9.

National Cancer Institute; Docetaxel, Oct. 5, 2006, hereafter will be referred as NCI.

Japanese Office Action dated Apr. 11, 2017, in Japanese Patent Application No. 2015-539418 (with English Translation).

\* cited by examiner

| Group | Dose (mg/kg/day) | T/C (%) | BWC(%) Mean ± S.D. |
|---|---|---|---|
| Control | - | 100 | 3.8 ± 2.7 |
| Docetaxel | 15.0 | 86 | 2.7 ± 2.0 |
| Docetaxel | 30.0 | 63 | 7.7 ± 3.0 |
| Compound 1 | 5.0 | 72 | 5.0 ± 3.1 |
| Compound 1 | 10.0 | 44 | 3.9 ± 2.1 |
| Docetaxel/Compound 1 | 15.0 / 5.0 | 43 | 5.5 ± 2.3 |
| Docetaxel/Compound 1 | 15.0 / 10.0 | 22 | 2.5 ± 9.1 |
| Docetaxel/Compound 1 | 30.0 / 5.0 | 23 | 0.7 ± 5.3 |
| Docetaxel/Compound 1 | 30.0 / 10.0 | 16 | -9.6 ± 15.6 |

| Group | Dose (mg/kg/day) | T/C (%) | BWC(%) Mean ± S.D. |
|---|---|---|---|
| Control | - | 100 | 5.8 ± 5.5 |
| Paclitaxel | 15.0 | 70 | 8.2 ± 2.8 |
| Paclitaxel | 30.0 | 41 | 8.5 ± 3.1 |
| Paclitaxel | 60.0 | 24 | 8.1 ± 3.1 |
| Compound 1 | 5.0 | 63 | 4.6 ± 3.2 |
| Paclitaxel/Compound 1 | 15.0/5.0 | 45 | 4.4 ± 4.6 |
| Paclitaxel/Compound 1 | 30.0/5.0 | 28 | 7.0 ± 3.5 |
| Paclitaxel/Compound 1 | 60.0/5.0 | 17 | 5.5 ± 3.3 |

| Group | Dose (mg/kg/day) | Schedule (day) | T/C (%) | BWC(%) Mean ± S.D. |
|---|---|---|---|---|
| Control | - | - | 100 | 6.5 ± 2.0 |
| Cisplatin | 7.0 | 1 | 65 | 5.6 ± 3.6 |
| Compound 1 | 5.0 | 1-14 | 51 | 6.5 ± 6.9 |
| Compound 1 | 10.0 | 1,3,5,8,10,12 | 54 | 3.1 ± 2.7 |
| Compound 1 | 20.0 | 1,4,8,11 | 46 | 2.7 ± 3.2 |
| Cisplatin/Compound 1 | 7.0/5.0 | 1/1-14 | 26 | 4.7 ± 7.5 |
| Cisplatin/Compound 1 | 7.0/10.0 | 1/1,3,5,8,10,12 | 26 | 3.6 ± 3.0 |
| Cisplatin/Compound 1 | 7.0/20.0 | 1/1,4,8,11 | 25 | 3.5 ± 5.3 |

| Group | Dose (mg/kg/day) | T/C (%) | BWC(%) Mean ± S.D. |
|---|---|---|---|
| Control | - | 100 | 7.8 ± 4.6 |
| Amrubicin | 12.5 | 40 | 8.0 ± 3.2 |
| Compound 1 | 20.0 | 62 | 5.9 ± 3.8 |
| Compound 1 | 28.0 | 49 | 5.4 ± 6.5 |
| Amrubicin/Compound 1 | 12.5/20.0 | 21 | 5.3 ± 2.0 |
| Amrubicin/Compound 1 | 12.5/28.0 | 17 | -0.6 ± 15.6 |

COMBINATION THERAPY USING AZABICYCLO COMPOUND FOR CANCER

CROSS REFERENCES TO RELATED APPLICATIONS

This application is a continuation of U.S. patent application Ser. No. 15/025,797, filed Mar. 29, 2016, which is the National Stage of the International Patent Application No. PCT/JP2014/075846, filed Sep. 29, 2014, the disclosures of which are incorporated herein by reference in their entireties. This application claims priority to Japanese Application No. 2013-205500, filed Sep. 30, 2013.

TECHNICAL FIELD

The present invention relates to an antitumor agent containing a combination of an azabicyclo compound or a salt thereof and other antitumor agent(s), and an antitumor effect potentiator for other antitumor agent(s).

BACKGROUND ART

A group of proteins called molecular chaperons is a multifunctional protein, which promotes the formation of the functional structures of other proteins or maintains these structures, promotes correct association, inhibits unnecessary aggregation, protects other proteins from degradation, and promotes secretion (Non Patent Literature 1). HSP90 is a molecular chaperon as abundant as approximately 1 to 2% of all intracellular soluble proteins and is however unnecessary for the biosynthesis of the majority of polypeptides, unlike other chaperon proteins (Non Patent Literature 1). Signaling-related factors (for example, ERBB1/EGFR, ERBB2/HER2, MET, IGF1R, KDR/VEGFR, FLT3, ZAP70, KIT, CHUK/IKK, BRAF, RAF1, SRC, and AKT), cell cycle regulators (for example, CDK4, CDK6, Cyclin D, PLK1, and BIRC5), and transcriptional regulators (for example, HIF-1α, p53, androgen receptor, estrogen receptor, and progesterone receptor) are known as the main client proteins whose structure formation or stability is regulated by HSP90 through the interaction therebetween (Non Patent Literatures 2 and 3). HSP90 is deeply involved in cell proliferation or survival by maintaining the normal functions of these proteins. Furthermore, HSP90 is required for the normal functions of mutated or chimeric factors (for example, BCR-ABL and NPM-ALK) which cause carcinogenesis or exacerbation of cancer. This indicates the importance of HSP90 particularly for processes such as carcinogenesis, cancer survival, growth, exacerbation, and metastasis (Non Patent Literature 2).

The inhibition of the chaperon functions of HSP90 by specific inhibitors such as geldanamycin causes the inactivation, destabilization, and degradation of the client proteins, resulting in induction of a halt in cell proliferation or apoptosis (Non Patent Literature 4). In terms of the physiological functions of HSP90, HSP90 inhibitors are characterized in that they can simultaneously inhibit multiple signaling pathways involved in cancer survival and growth. Thus, the HSP90 inhibitors can serve as pharmaceuticals having extensive and effective anticancer activity. Moreover, from the findings that cancer cell-derived HSP90 has higher activity and higher affinity for ATP or inhibitors than those of normal cell-derived HSP90, it has been expected that the HSP90 inhibitors would serve as pharmaceuticals having high cancer selectivity (Non Patent Literature 5). Currently, the clinical development of multiple HSP90 inhibitors as anticancer agents is ongoing. The most advancing Ganetespib is under development as single agents as well as under test on the combined use with other antitumor agents such as docetaxel (Non Patent Literature 6).

Further, a new type of HSP90 inhibitor has been reported (Patent Literature 1), and HSP90 inhibitors with higher antitumor effects and reduced side effects have been desired.

CITATION LIST

Patent Literature

Patent Literature 1: WO 2011/004610 A

Non Patent Literatures

Non Patent Literature 1: Nature Reviews Cancer 5, 761-772 (2005)
Non Patent Literature 2: TRENDS in Molecular Medicine 10(6), 283-290 (2004)
Non Patent Literature 3: Clin Can Res 15, 9-14(2009)
Non Patent Literature 4: Current Opinion in Pharmacology 8, 370-374(2008)
Non Patent Literature 5: Drug Resistance Updates 12, 17-27 (2009)
Non Patent Literature 6: Invest New Drugs. 30(6):2201-9 (2012)

SUMMARY OF INVENTION

Technical Problem

An object of the invention is to provide a method of using HSP90 inhibitors with high antitumor effects and reduced side effects.

Solution to Problem

The present inventors examined combined use of various HSP90 inhibitors and other antitumor agent(s) under the circumstances. As a result, they found that an azabicyclo compound having an HSP90 inhibitory agent remarkably potentiates the antitumor effect of extremely various ranges of antitumor agents having different action mechanisms.

That is, the invention provides the following [1] to [36].

[1] An antitumor agent, where an azabicyclo compound of the following Formula (I) or a salt thereof:

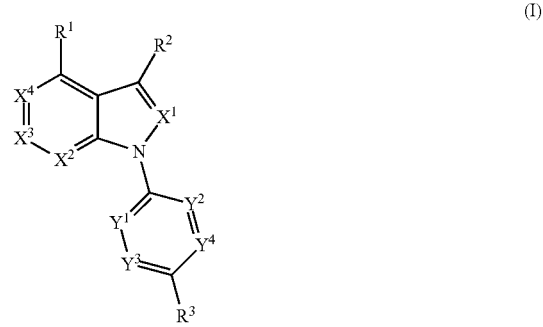

in the formula, $X^1$ represents CH or N;
any one of $X^2$, $X^3$, and $X^4$ is N, and the others represent CH;

any one or two of $Y^1$, $Y^2$, $Y^3$, and $Y^4$ are C—$R^4$, and the others are the same or different and represent CH or N;

$R^1$ represents an optionally substituted mono- or bi-cyclic unsaturated heterocyclic group having 1 to 4 of heteroatom selected from the group consisting of N, S, and O;

$R^2$ represents a hydrogen atom, an optionally substituted alkyl group having 1 to 6 of carbon atom, or an optionally substituted alkenyl group having 2 to 6 of carbon atom;

$R^3$ represents a cyano group or —CO—$R^5$;

$R^4$(s) are the same or different and represent a hydrogen atom, a halogen atom, a cyano group, an optionally substituted alkyl group having 1 to 6 of carbon atom, an alkenyl group having 2 to 6 of carbon atom, an alkoxy group having 1 to 6 of carbon atom, an aromatic hydrocarbon group, —N($R^6$)($R^7$), —S—$R^8$, or —CO—$R^9$;

$R^5$ represents an amino group optionally having a hydroxyl group or an optionally substituted mono- or di-alkylamino group;

$R^6$ and $R^7$ are the same or different and represent a hydrogen atom, an optionally substituted alkyl group having 1 to 6 of carbon atom, a halogenoalkyl group having 1 to 6 of carbon atom, an optionally substituted cycloalkyl group having 3 to 7 of carbon atom, an optionally substituted aralkyl group, an optionally substituted aromatic hydrocarbon group, an optionally substituted saturated heterocyclic group, or an optionally substituted unsaturated heterocyclic group, or $R^6$ and $R^7$ optionally form a saturated heterocyclic group together with a nitrogen atom to which they are bonded;

$R^8$ represents an optionally substituted cycloalkyl group having 3 to 7 of carbon atom or an optionally substituted aromatic hydrocarbon group; and $R^9$ represents a hydrogen atom, a hydroxyl group, an amino group optionally having a hydroxyl group, or an optionally substituted mono- or di-alkylamino group, is administered in combination with other antitumor agent(s).

[2] The antitumor agent according to [1], where
the azabicyclo compound is a compound of Formula (I),
in the formula, $X^1$ is CH or N;
$X^2$ is N and $X^3$ and $X^4$ are CH;
$Y^1$ and $Y^3$ are CH, any one or two of $Y^2$ and $Y^4$ are C—$R^4$, and the other is CH;

$R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group;

$R^2$ is an alkyl group having 1 to 6 of carbon atom optionally having a halogen atom or an alkenyl group having 2 to 6 of carbon atom;

$R^3$ is —CO—$R^5$;

$R^4$ is a halogen atom, an alkyl group having 1 to 6 of carbon atom optionally having a mono- or di-(C1-C6 alkyl) amino group or a monocyclic 5- to 7-membered saturated heterocyclic group having one or two of any heteroatom of N, S, and O, an alkoxy group having 1 to 6 of carbon atom, —N($R^6$)($R^7$), —S$R^8$, or —CO—$R^9$;

$R^5$ is an amino group or mono- or di-(C1-C6 alkyl)amino group;

$R^6$ is a hydrogen atom or an optionally substituted alkyl group having 1 to 6 of carbon atom;

$R^7$ is a hydrogen atom, an optionally substituted alkyl group having 1 to 6 of carbon atom, an optionally substituted cycloalkyl group having 3 to 7 of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or $R^6$ and $R^7$ form a 5- to 7-membered saturated heterocyclic group together with a nitrogen atom to which they are bonded;

$R^8$ is an optionally substituted cycloalkyl group having 3 to 7 of carbon atom or an optionally substituted aromatic hydrocarbon group having 6 to 14 of carbon atom; and $R^9$ is a hydrogen atom, a hydroxyl group, an amino group, or a mono- or di-(C1-C6 alkyl)amino group.

[3] The antitumor agent according to [1] or [2], where the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[4] The antitumor agent according to any one of [1] to [3], where the other antitumor agent is one or more of kind(s) selected from the group consisting of an antitumor antibiotic substance, a platinum-based agent, a pyrimidine-based antimetabolite agent, a purine-based antimetabolite agent, a folic acid antimetabolite agent, a plant alkaloid-based antitumor agent, an immunomodulating drug, and a low molecular weight molecular targeted drug.

[5] The antitumor agent according to any one of [1] to [4], where the other antitumor agent is one or more of kind(s) selected from the group consisting of amrubicin, doxorubicin, cisplatin, oxaliplatin, gemcitabine, cytarabine, pemetrexed, paclitaxel (for example, TAXOL or ABRAXANE), docetaxel, etoposide, lenalidomide, imatinib, gefitinib, dasatinib, erlotinib, lapatinib, and crizotinib.

[6] The antitumor agent according to any one of [1] to [5], where the azabicyclo compound or a salt thereof and the other antitumor agent are administered to a cancer patient simultaneously or separately at an interval.

[7] An antitumor effect potentiator for other antitumor agent(s), containing an azabicyclo compound or a salt thereof, in which
the azabicyclo compound is a compound of the following Formula (I):

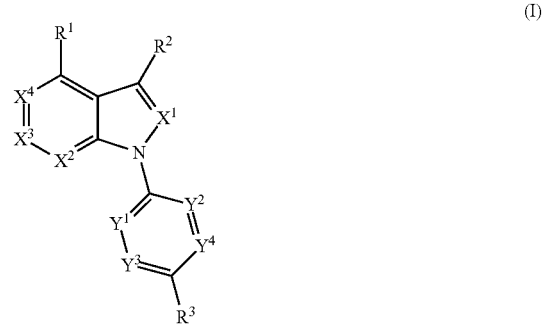

in the formula, $X^1$ to $X^4$, $Y^1$ to $Y^4$, and $R^1$ to $R^3$ are as defined above.

[8] An antitumor agent containing an azabicyclo compound or a salt thereof, which is used for treating a cancer patient who has been administered other antitumor agent(s), in which the azabicyclo compound is an azabicyclo compound of the following Formula (I):

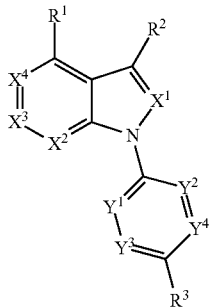

(I)

in the formula, $X^1$ to $X^4$, $Y^1$ to $Y^4$, $R^1$ to $R^3$ are as defined above.

[9] An antitumor agent containing a combination of an azabicyclo compound or a salt thereof and other antitumor agent(s), in which
the azabicyclo compound is an azabicyclo compound of the following Formula (I):

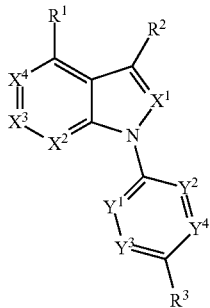

(I)

in the formula, $X^1$ to $X^4$, $Y^1$ to $Y^4$, $R^1$ to $R^3$ are as defined above.

[10] An azabicyclo compound of the following Formula (I) or a salt thereof:

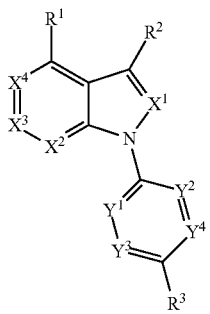

(I)

in the formula, $X^1$ to $X^4$, $Y^1$ to $Y^4$, $R^1$ to $R^3$ are as defined above,
which is used for treating a tumor by administration in combination with other antitumor agent(s).

[11] The compound according to [10] or a salt thereof, where the azabicyclo compound is a compound of Formula (I), in the formula, $X^1$ is CH or N;
$X^2$ is N and $X^3$ and $X^4$ are CH;
$Y^1$ and $Y^3$ are CH, any one or two of $Y^2$ and $Y^4$ are C—$R^4$, and the other is CH;
$R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group;
$R^2$ is an alkyl group having 1 to 6 of carbon atom optionally having a halogen atom or an alkenyl group having 2 to 6 of carbon atom;
$R^3$ is —CO—$R^5$;
$R^4$ is a halogen atom, an alkyl group having 1 to 6 of carbon atom optionally having a mono- or di-(C1-C6 alkyl) amino group or a monocyclic 5- to 7-membered saturated heterocyclic group having one or two of any heteroatom of N, S, and O, an alkoxy group having 1 to 6 of carbon atom, —N($R^6$) ($R^7$), —S$R^8$, or —CO—$R^9$;
$R^5$ is an amino group or mono- or di-(C1-C6 alkyl)amino group;
$R^6$ is a hydrogen atom or an optionally substituted alkyl group having 1 to 6 of carbon atom;
$R^7$ is a hydrogen atom, an optionally substituted alkyl group having 1 to 6 of carbon atom, an optionally substituted cycloalkyl group having 3 to 7 of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or $R^6$ and $R^7$ form a 5- to 7-membered saturated heterocyclic group together with a nitrogen atom to which they are bonded;
$R^8$ is an optionally substituted cycloalkyl group having 3 to 7 of carbon atom or an optionally substituted aromatic hydrocarbon group having 6 to 14 of carbon atom; and
$R^9$ is a hydrogen atom, a hydroxyl group, an amino group, or a mono- or di-(C1-C6 alkyl)amino group.

[12] The compound according to [10] or [11] or a salt thereof, where the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[13] The compound according to any one of [10] to [12] or a salt thereof, where the other antitumor agent is one or more of kind(s) selected from the group consisting of an antitumor antibiotic substance, a platinum-based agent, a pyrimidine-based antimetabolite agent, a purine-based antimetabolite agent, a folic acid antimetabolite agent, a plant alkaloid-based antitumor agent, an immunomodulating drug, and a low molecular weight molecular targeted drug.

[14] The compound according to any one of [10] to [13] or a salt thereof, where the other antitumor agent is one or more of kind(s) selected from the group consisting of amrubicin, doxorubicin, cisplatin, oxaliplatin, gemcitabine, cytarabine, pemetrexed, paclitaxel (for example, TAXOL or ABRAXANE), docetaxel, etoposide, lenalidomide, imatinib, gefitinib, dasatinib, erlotinib, lapatinib, and crizotinib.

[15] The compound according to any one of [10] to [14] or a salt thereof, where the azabicyclo compound or a salt thereof and the other antitumor agent are administered to a cancer patient simultaneously or separately at an interval.

[16] A compound of the following Formula (I) or a salt thereof:

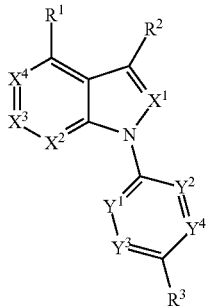

in the formula, $X^1$ to $X^4$, $Y^1$ to $Y^4$, $R^1$ to $R^3$ are as defined above,
which is used for potentiating the antitumor effect of other antitumor agent(s).

[17] An azabicyclo compound of the following Formula (I) or a salt thereof, which is used for treating a cancer patient who has been administered other antitumor agent(s):

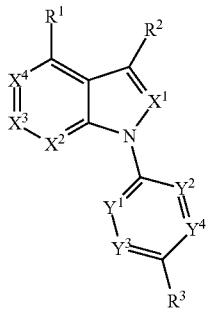

in the formula, $X^1$ to $X^4$, $Y^1$ to $Y^4$, $R^1$ to $R^3$ are as defined above.

[18] An azabicyclo compound of the following Formula (I) or a salt thereof:

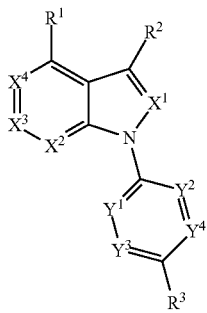

in the formula, $X^1$ to $X^4$, $Y^1$ to $Y^4$, $R^1$ to $R^3$ are as defined above,
which is used for treating a tumor in combination with other antitumor agent(s).

[19] Use of an azabicyclo compound of the following Formula (I) or a salt thereof:

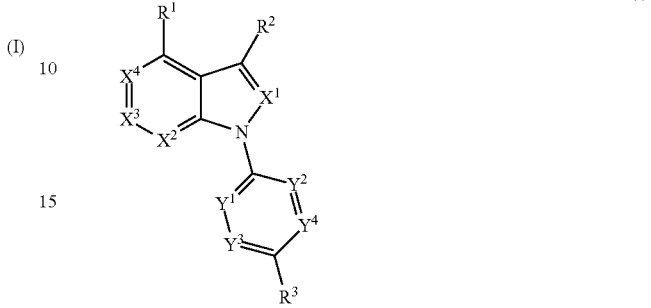

in the formula, $X^1$ to $X^4$, $Y^1$ to $Y^4$, $R^1$ to $R^3$ are as defined above,
which is used for producing an antitumor agent to be administered in combination with other antitumor agent(s).

[20] The use according to [19], where
the azabicyclo compound is a compound of Formula (I),
in the formula, $X^1$ is CH or N;
$X^2$ is N and $X^3$ and $X^4$ are CH;
$Y^1$ and $Y^3$ are CH, any one or two of $Y^2$ and $Y^4$ are C—$R^4$, and the other is CH;
$R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group;
$R^2$ is an alkyl group having 1 to 6 of carbon atom optionally having a halogen atom or an alkenyl group having 2 to 6 of carbon atom;
$R^3$ is —CO—$R^5$;
$R^4$ is a halogen atom, an alkyl group having 1 to 6 of carbon atom optionally having a mono- or di-(C1-C6 alkyl) amino group or a monocyclic 5- to 7-membered saturated heterocyclic group having one or two of any heteroatom of N, S, and O, an alkoxy group having 1 to 6 of carbon atom, —N($R^6$)($R^7$), —S$R^8$, or —CO—$R^9$;
$R^5$ is an amino group or mono- or di-(C1-C6 alkyl)amino group;
$R^6$ is a hydrogen atom or an optionally substituted alkyl group having 1 to 6 of carbon atom;
$R^7$ is a hydrogen atom, an optionally substituted alkyl group having 1 to 6 of carbon atom, an optionally substituted cycloalkyl group having 3 to of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or $R^6$ and $R^7$ form a 5- to 7-membered saturated heterocyclic group together with a nitrogen atom to which they are bonded;

R[8] is an optionally substituted cycloalkyl group having 3 to 7 of carbon atom or an optionally substituted aromatic hydrocarbon group having 6 to 14 of carbon atom; and R[9] is a hydrogen atom, a hydroxyl group, an amino group, or a mono- or di-(C1-C6 alkyl)amino group.

[21] The use according to [19] or [20], where the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[22] The use according to any one of [19] to [21], where the other antitumor agent is one or more of kind(s) selected from the group consisting of an antitumor antibiotic substance, a platinum-based agent, a pyrimidine-based antimetabolite agent, a purine-based antimetabolite agent, a folic acid antimetabolite agent, a plant alkaloid-based antitumor agent, an immunomodulating drug, and a low molecular weight molecular targeted drug.

[23] The use according to any one of [19] to [22], where the other antitumor agent is one or more of kind(s) selected from the group consisting of amrubicin, doxorubicin, cisplatin, oxaliplatin, gemcitabine, cytarabine, pemetrexed, paclitaxel (for example, TAXOL or ABRAXANE), docetaxel, etoposide, lenalidomide, imatinib, gefitinib, dasatinib, erlotinib, lapatinib, and crizotinib.

[24] The use according to any one of [19] to [23], where the azabicyclo compound or a salt thereof and the other antitumor agent are administered to a cancer patient simultaneously or separately at an interval.

[25] Use of a compound of the following Formula (I) or a salt thereof:

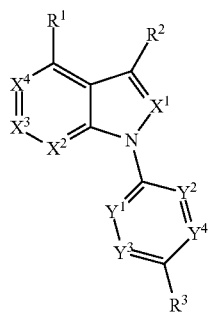

(I)

in the formula, $X^1$ to $X^4$, $Y^1$ to $Y^4$, $R^1$ to $R^3$ are as defined above,
which is used for producing an antitumor effect potentiator for other antitumor agent(s).

[26] Use of an azabicyclo compound of the following Formula (I) or a salt thereof:

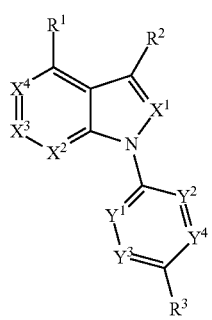

(I)

in the formula, $X^1$ to $X^4$, $Y^1$ to $Y^4$, $R^1$ to $R^3$ are as defined above,
which is used for producing an antitumor agent for treating a cancer patient who has been administered other antitumor agent(s).

[27] Use of an azabicyclo compound of the following Formula (I) or a salt thereof:

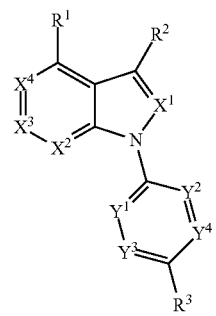

(I)

in the formula, $X^1$ to $X^4$, $Y^1$ to $Y^4$, $R^1$ to $R^3$ are as defined above,
which is used for producing an antitumor agent by combining other antitumor agent(s).

[28] A method for treating a tumor, including administrating an azabicyclo compound of the following Formula (I) or a salt thereof:

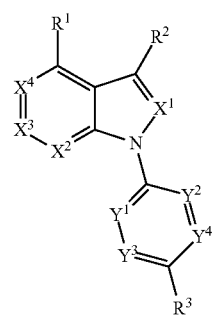

(I)

in the formula, $X^1$ to $X^4$, $Y^1$ to $Y^4$, $R^1$ to $R^3$ are as defined above,
and other antitumor agent(s), in combination.

[29] The treating method according to [28], where
the azabicyclo compound is a compound of Formula (I),
in the formula, $X^1$ is CH or N;
$X^2$ is N and $X^3$ and $X^4$ are CH;
$Y^1$ and $Y^3$ are CH, any one or two of $Y^2$ and $Y^4$ are C—$R^4$, and the other is CH;
$R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group;

R² is an alkyl group having 1 to 6 of carbon atom optionally having a halogen atom or an alkenyl group having 2 to 6 of carbon atom;

R³ is —CO—R⁵;

R⁴ is a halogen atom, an alkyl group having 1 to 6 of carbon atom optionally having a mono- or di-(C1-C6 alkyl) amino group or a monocyclic 5- to 7-membered saturated heterocyclic group having one or two of any heteroatom of N, S, and O, an alkoxy group having 1 to 6 of carbon atom, —N(R⁶)(R⁷), —SR⁸, or —CO—R⁹;

R⁵ is an amino group or mono- or di-(C1-C6 alkyl)amino group;

R⁶ is a hydrogen atom or an optionally substituted alkyl group having 1 to 6 of carbon atom;

R⁷ is a hydrogen atom, an optionally substituted alkyl group having 1 to 6 of carbon atom, an optionally substituted cycloalkyl group having 3 to 7 of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or R⁶ and R⁷ form a 5- to 7-membered saturated heterocyclic group together with a nitrogen atom to which they are bonded;

R⁸ is an optionally substituted cycloalkyl group having 3 to 7 of carbon atom or an optionally substituted aromatic hydrocarbon group having 6 to 14 of carbon atom; and R⁹ is a hydrogen atom, a hydroxyl group, an amino group, or a mono- or di-(C1-C6 alkyl)amino group.

[30] The treating method according to [28], where the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[31] The treating method according to [28], where the other antitumor agent is one or more of kind(s) selected from the group consisting of an antitumor antibiotic substance, a platinum-based agent, a pyrimidine-based antimetabolite agent, a purine-based antimetabolite agent, a folic acid antimetabolite agent, a plant alkaloid-based antitumor agent, an immunomodulating drug, and a low molecular weight molecular targeted drug.

[32] The treating method according to [28], where the other antitumor agent is one or more of kind(s) selected from the group consisting of amrubicin, doxorubicin, cisplatin, oxaliplatin, gemcitabine, cytarabine, pemetrexed, paclitaxel (for example, TAXOL or ABRAXANE), docetaxel, etoposide, lenalidomide, imatinib, gefitinib, dasatinib, erlotinib, lapatinib, and crizotinib.

[33] The treating method according to any one of [28] to [32], where the azabicyclo compound or a salt thereof and the other antitumor agent are administered to a cancer patient simultaneously or separately at an interval.

[34] A method for potentiating the antitumor effect of other antitumor agent(s), including administering an azabicyclo compound or a salt thereof, in which the azabicyclo compound is a compound of the following Formula (I):

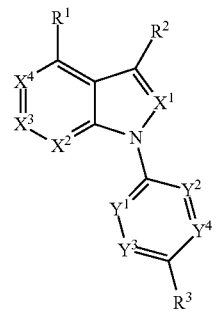

in the formula, X¹ to X⁴, Y¹ to Y⁴, R¹ to R³ are as defined above.

[35] A method for treating a tumor, including administering an azabicyclo compound or a salt thereof to a cancer patient who has been administered other antitumor agent(s), in which the azabicyclo compound is an azabicyclo compound of the following Formula (I):

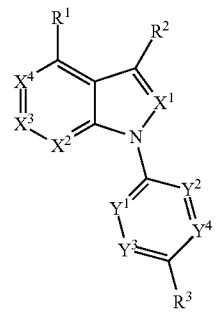

in the formula, X¹ to X⁴, Y¹ to Y⁴, R¹ to R³ are as defined above.

[36] A method for treating a tumor, including administering an azabicyclo compound or a salt thereof and other antitumor agent(s), in combination, in which the azabicyclo compound is an azabicyclo compound of the following Formula (I):

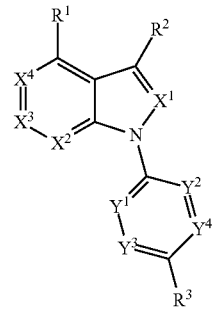

in the formula, X¹ to X⁴, Y¹ to Y⁴, R¹ to R³ are as defined above.

Advantageous Effects of Invention

The antitumor agent of the invention serves to perform cancer therapy exhibiting high antitumor effect while suppressing side effects, and, thus, the survival of a cancer patient can be prolonged.

DESCRIPTION OF EMBODIMENTS

Figure 1:
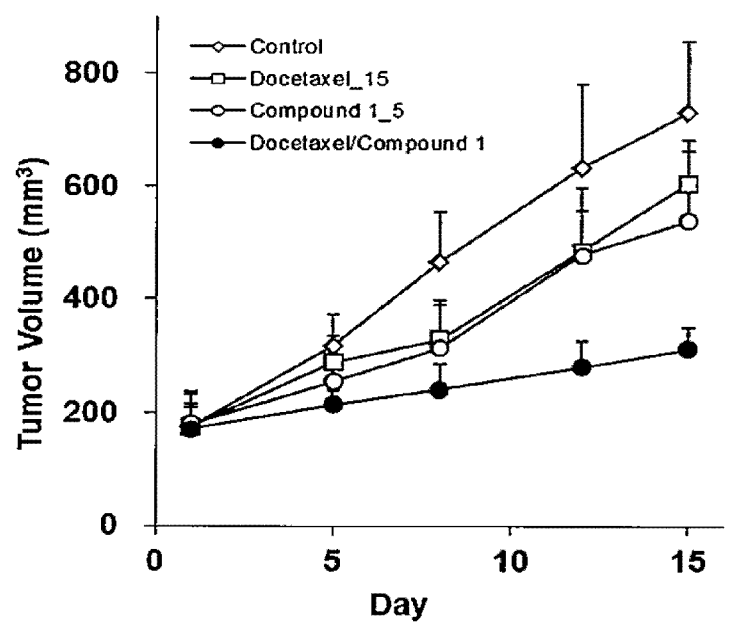
FIG. 1 shows an effect of the combination of Compound 1 and docetaxel with respect to the rate of tumor growth of a human non-small cell lung cancer line NCI-H2170.

The HSP90 inhibitor in the invention, which provides an excellent synergic effect with other antitumor agent(s), is an azabicyclo compound of the following Formula (I) and a salt thereof.

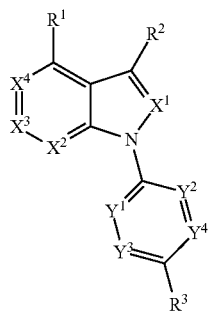

(I)

in the formula, $X^1$ to $X^4$, $Y^1$ to $Y^4$, $R^1$ to $R^3$ are as defined above.

In the present specification, examples of "substituents" include a halogen atom, a hydroxyl group, a cyano group, a nitro group, an alkyl group, a halogenoalkyl group, a cycloalkyl group, a cycloalkyl-alkyl group, an aralkyl group, a hydroxyalkyl group, an alkenyl group, an alkynyl group, an alkoxy group, a halogenoalkoxy group, an alkoxy-alkyl group, a cycloalkoxy group, a cycloalkyl-alkoxy group, an aralkyloxy group, an aralkyloxy-alkyl group, an alkylthio group, a cycloalkyl-alkylthio group, an amino group, a mono- or dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group, and a saturated heterocyclic oxy group. When the above substituent is present, the number of the substituents is typically 1 to 3.

Examples of the halogen atom included in the substituents include a chlorine atom, a bromine atom, fluorine atom, and an iodine atom.

The alkyl group or the halogenoalkyl group included in the substituents preferably refers to a linear or branched alkyl group having 1 to 6 of carbon atom or a group in which one or all hydrogen atom(s) in such an alkyl group are substituted by the halogen atom described above. Examples thereof include alkyl groups such as a methyl group, an ethyl group, an n-propyl group, an isopropyl group, an n-butyl group, an isobutyl group, a sec-butyl group, a tert-butyl group, a pentyl group, and a hexyl group and halogenoalkyl groups such as a trifluoromethyl group.

The cycloalkyl group included in the substituents is preferably a cycloalkyl group having 3 to 7 of carbon atom, and examples thereof include a cyclopropyl group, a cyclobutyl group, a cyclopentyl group, a cyclohexyl group, and a cycloheptyl group.

The cycloalkyl-alkyl group included in the substituents is preferably an alkyl group having 1 to 6 of carbon atom which is substituted by cycloalkyl having 3 to 7 of carbon atom, and examples thereof include a cyclopropylmethyl group, a cyclopropylethyl group, a cyclobutylmethyl group, a cyclopentylmethyl group, and a cyclohexylmethyl group.

The aralkyl group included in the substituents preferably refers to a linear or branched alkyl group having 1 to 6 of carbon atom which is substituted by an aromatic hydrocarbon group having 6 to 14 of carbon atom, and examples thereof include a benzyl group, a phenylethyl group, a phenylpropyl group, a naphthylmethyl group, and a naphthylethyl group.

The hydroxyalkyl group included in the substituents preferably refers to the linear or branched alkyl group having 1 to 6 of carbon atom described which has a hydroxy group, and examples thereof include a hydroxymethyl group and a hydroxyethyl group.

The alkenyl group included in the substituents preferably refers to an alkenyl group having 2 to 6 of carbon atom which contains a carbon-carbon double bond, and examples thereof include a vinyl group, an allyl group, a methylvinyl group, a propenyl group, a butenyl group, a pentenyl group, and a hexenyl group.

The alkynyl group included in the substituents preferably refers to an alkynyl group having 2 to 6 of carbon atom which contains a carbon-carbon triple bond, and examples thereof include an ethynyl group and a propargyl group.

The alkoxy group or the halogenoalkoxy group included in the substituents preferably refers to a linear or branched alkoxy group having 1 to 6 of carbon atom, or a group in which such an alkoxy group is substituted by the halogen atom described above, and examples thereof include a methoxy group, an ethoxy group, an n-propoxy group, an isopropoxy group, a 1-methylpropoxy group, an n-butoxy group, an isobutoxy group, a tert-butoxy group, a 2-methylbutoxy group, a neopentyloxy group, a pentan-2-yloxy group, a fluoromethoxy group, a difluoromethoxy group, a trifluoromethoxy group, a 1,1-difluoroethoxy group, a 2,2-difluoroethoxy group, a 2,2,2-trifluoroethoxy group, a 1,1,2,2-tetrafluoroethoxy group, a perfluoroethoxy group, a 3-fluoro-2-(fluoromethyl)-propoxy group, a 1,3-difluoropropan-2-yloxy group, and a 2,2,3,3,3-pentafluoro-1-propoxy group.

The cycloalkoxy group included in the substituents is preferably a cycloalkoxy group having 3 to 7 of carbon atom, and examples thereof include a cyclopropoxy group, a cyclobutoxy group, a cyclopentyloxy group, a cyclohexyloxy group, and a cycloheptyloxy group.

The alkoxy-alkyl group included in the substituents preferably refers to the alkyl group having 1 to 6 of carbon atom described above which is substituted by the linear or branched alkoxy group having 1 to 6 of carbon atom described above, and examples thereof include a methoxymethyl group and an ethoxymethyl group.

The cycloalkyl-alkoxy group included in the substituents is preferably an alkoxy group having 1 to 6 of carbon atom which is substituted by cycloalkyl having 3 to 7 of carbon atom, and examples thereof include a cyclopropylmethoxy group, a cyclopropylethoxy group, a cyclobutylmethoxy group, a cyclopentylmethoxy group, and a cyclohexylmethoxy group.

The aralkyloxy group included in the substituents preferably refers to an oxy group which has the aralkyl group described above, and examples thereof include a benzyloxy group, a phenethyloxy group, a phenylpropyloxy group, a naphthylmethyloxy group, and a naphthylethyloxy group.

The aralkyloxy-alkyl group included in the substituents preferably refers to the linear or branched alkyl group having 1 to 6 of carbon atom described above which has the aralkyloxy group described above, and examples thereof include a benzyloxymethyl group and a benzyloxyethyl group.

The alkylthio group included in the substituents is preferably a (C1-C6) alkylthio group which refers to a linear or branched alkylthio group having 1 to 6 of carbon atom, and examples thereof include a methylthio group, an ethylthio group, an n-propylthio group, an isopropylthio group, an n-butylthio group, an isobutylthio group, a sec-butylthio group, a tert-butylthio group, a pentylthio group, and a hexylthio group.

The cycloalkyl-alkylthio group included in the substituents is preferably an alkylthio group having 1 to 6 of carbon atom which is substituted by cycloalkyl having 3 to 7 of carbon atom, and examples thereof include a cyclopropylmethylthio group, a cyclopropylethylthio group, a cyclobutylmethylthio group, a cyclopentylmethylthio group, and a cyclohexylmethylthio group.

The mono- or dialkylamino group included in the substituents is a mono- or di-(C1-C6 alkylamino group which refers to an amino group which is monosubstituted or disubstituted by the linear or branched alkyl group having 1 to 6 of carbon atom described above, and examples thereof include a methylamino group, a dimethylamino group, an ethylamino group, a diethylamino group, and a methylethylamino group.

The cycloalkyl-alkylamino group included in the substituents refers to an alkylamino group which is substituted by the cycloalkyl group described above, and examples thereof include a cyclopropylmethylamino group, a cyclobutylmethylamino group, and a cyclopentylmethylamino group.

Examples of the acyl group included in the substituents include: linear or branched acyl groups having 1 to 6 of carbon atom such as a formyl group, an acetyl group, a propionyl group, an n-butyryl group, an isobutyryl group, a valeryl group, an isovaleryl group, and a pivaloyl group; and a benzoyl group.

Examples of the acyloxy group included in the substituents include: linear or branched acyloxy groups having 1 to 6 of carbon atom such as a formyloxy group, an acetoxy group, a propionyloxy group, an n-butyryloxy group, an isobutyryloxy group, a valeryloxy group, an isovaleryloxy group, and a pivaloyloxy group; a benzoyloxy group; and amino acid-derived acyloxy groups such as a glycyloxy group, an alanyloxy group, and a leucyloxy group.

The alkoxycarbonyl group included in the substituents refers to a carbonyl group which is substituted by the alkoxy group described above, and examples thereof include a methoxycarbonyl group, an ethoxycarbonyl group, an n-propoxycarbonyl group, an isopropoxycarbonyl group, a 1-methylpropoxycarbonyl group, an n-butoxycarbonyl group, an isobutoxycarbonyl group, a tert-butoxycarbonyl group, a 2-methyl-butoxycarbonyl group, a neopentyloxycarbonyl group, and a pentan-2-yloxycarbonyl group.

The aralkyloxycarbonyl group included in the substituents preferably refers to a carbonyl group which is substituted by the aralkyloxy group described above, and examples thereof include a benzyloxycarbonyl group, a phenethyloxycarbonyl group, a phenylpropyloxycarbonyl group, a naphthylmethyloxycarbonyl group, and a naphthylethyloxycarbonyl group.

Examples of the carbamoyl group in the substituents include a —$CONH_2$ group, a (mono- or dialkyl)carbamoyl group, a (mono- or diaryl)carbamoyl group, an (N-alkyl-N-aryl)carbamoyl group, a pyrrolidinocarbamoyl group, piperidinocarbamoyl group, a piperidinocarbamoyl group, and a morpholinocarbamoyl group.

The saturated or unsaturated heterocyclic group included in the substituents refers to a mono- or bi-cyclic saturated or 5- to 10-membered unsaturated heterocyclic group preferably having 1 to 4 of any heteroatom of N, S and O, and examples thereof include a pyrrolidinyl group, a piperidinyl group, a piperazinyl group, a hexamethyleneimino group, a morpholino group, a thiomorpholino group, a homopiperazinyl group, tetrahydrofuranyl group, a tetrahydropyranyl group, an imidazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a methylenedioxyphenyl group, an ethylenedioxyphenyl group, a benzofuranyl group, a dihydrobenzofuranyl group, a benzoimidazolyl group, a benzooxazolyl group, a benzothiazolyl group, a purinyl group, a quinolyl group, an isoquinolyl group, a quinazolinyl group, and a quinoxalyl group.

The aromatic hydrocarbon group included in the substituents preferably refers to an aromatic hydrocarbon group having 6 to 14 of carbon atom, and examples thereof include a phenyl group and a naphthyl group.

The saturated heterocyclic oxy group included in the substituents refers to a monocyclic 5- to 7-membered saturated heterocyclic group having one or two of any heteroatom of N, S and O, for example, an oxy group which has a pyrrolidinyl group, a piperidinyl group, a piperazinyl group, a hexamethyleneimino group, a morpholino group, a thiomorpholino group, or a homopiperazinyl group. Examples thereof include a tetrahydrofuranyloxy group and a tetrahydropyranyloxy group.

In Formula (I), $X^1$ represents CH or N. Moreover, in Formula (I), any one of $X^2$, $X^3$, and $X^4$ represents N, and the others represent CH. Based on these definitions of $X^1$ to $X^4$, examples of the azabicyclo skeleton in Formula (I) include the following structures:

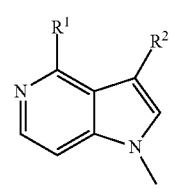

(A-1)

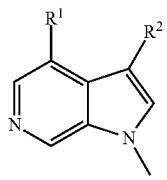
(A-2)

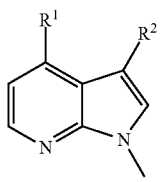
(A-3)

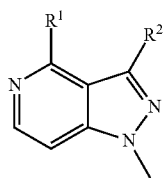
(A-4)

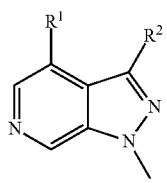
(A-5)

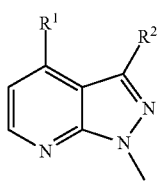
(A-6)

in the formula, $R^1$ and $R^2$ are as defined above.

Among these skeletons, (A-3) and (A-6) are particularly preferable.

In Formula (I), the "mono- or bi-cyclic unsaturated heterocyclic group having 1 to 4 of heteroatom selected from the group consisting of N, S, and O" in the "optionally substituted mono- or bi-cyclic unsaturated heterocyclic group having 1 to 4 of heteroatom selected from the group consisting of N, S, and O" represented by $R^1$ is preferably a mono- or bi-cyclic 5- to 10-membered unsaturated heterocyclic group having 1 to 3 of heteroatom selected from the group consisting of N, S, and O, more preferably a monocyclic 5- to 6-membered unsaturated heterocyclic group having 1 to 3 of heteroatom selected from the group consisting of N, S, and O, or a bicyclic 9- to 10-membered unsaturated heterocyclic group having 1 to 3 of heteroatom selected from the group consisting of N, S, and O. The heterocyclic group is preferably a group having imidazole, pyrazole, thiophene, furan, pyrrole, oxazole, isoxazole, thiazole, isothiazole, triazole, tetrazole, pyridine, pyrazine, pyrimidine, pyridazine, indole, isoindole, pyrrolopyridine, indazole, methylenedioxyphenyl, ethylenedioxyphenyl, benzofuran, dihydrobenzofuran, benzimidazol, benzoxazol, benzothiazole, purine, quinoline, tetrahydroquinoline, isoquinoline, quinazoline, or quinoxaline, more preferably a group having imidazol, pyrazol, thiophene, furan, pyridine, indole, pyrrolopyridine, benzofuran, quinoline, or tetrahydroquinoline, and particularly preferably a group having imidazol, pyridine, or quinoline.

Specific examples thereof include a 1H-imidazol-1-yl group, a 1H-imidazol-2-yl group, a 1H-imidazol-4-yl group, a 1H-pyrazol-1-yl group, a 1H-pyrazol-3-yl group, a 1H-pyrazol-4-yl group, a thiophen-2-yl group, a thiophen-3-yl group, a furan-2-yl group, a furan-3-yl group, a pyrrol-1-yl group, a pyrrol-2-yl group, a pyrrol-3-yl group, an oxazol-2-yl group, an oxazol-4-yl group, an oxazol-5-yl group, an isoxazol-3-yl group, an isoxazol-4-yl group, an isoxazol-5-yl group, a thiazol-2-yl group, a thiazol-3-yl group, a thiazol-4-yl group, a thiazol-5-yl group, an isothiazol-2-yl group, an isothiazol-4-yl group, an isothiazol-5-yl group, a pyrazol-1-yl group, a pyrazol-3-yl group, a pyrazol-4-yl group, a 1,2,3-triazol-1-yl group, a 1,2,3-triazol-4-yl group, a 1,2,4-triazol-1-yl group, a 1,2,4-triazol-3-yl group, a 1,2,4-triazol-4-yl group, tetrazol-1-yl group, a tetrazol-5-yl group, a pyridin-2-yl group, a pyridin-3-yl group, a pyridin-4-yl group, a pyrazin-2-yl group, a pyrazin-3-yl group, a pyrimidin-2-yl group, a pyrimidin-4-yl group, a pyrimidin-5-yl group, a pyrimidin-6-yl group, a pyridazin-3-yl group, a pyridazin-4-yl group, an indol-1-yl group, an indol-2-yl group, an indol-3-yl group, an indol-4-yl group, an indol-5-yl group, an indol-6-yl group, an indol-7-yl group, an isoindol-1-yl group, an isoindol-2-yl group, an isoindol-4-yl group, an isoindol-5-yl group, a 1H-pyrrolo[2,3-b]pyridin-1-yl group, a 1H-pyrrolo[2,3-b]pyridin-2-yl group, a 1H-pyrrolo[2,3-b]pyridin-3-yl group, a 1H-pyrrolo[2,3-b]pyridin-4-yl group, a 1H-pyrrolo[2,3-b]pyridin-5-yl group, a 1H-pyrrolo[2,3-b]pyridin-6-yl group, a 1H-indazol-1-yl group, a 1H-indazol-3-yl group, a 1H-indazol-4-yl group, a 1H-indazol-5-yl group, a 1H-indazol-6-yl group, a 1H-indazol-7-yl group, a methylenedioxyphenyl group, an, ethylenedioxyphenyl group, a benzofuran-2-yl group, a benzofuran-3-yl group, a benzofuran-4-yl group, a benzofuran-5-yl group, a benzofuran-6-yl group, a benzofuran-7-yl group, a 2,3-dihydrobenzofuran-2-yl group, a 2,3-dihydrobenzofuran-3-yl group, a benzimidazol-1-yl group, a benzimidazol-2-yl group, a benzimidazol-4-yl group, a benzimidazol-5-yl group, a benzoxazol-2-yl group, a benzoxazol-4-yl group, benzoxazol-5-yl group, a benzothiazol-2-yl group, benzothiazol-4-yl group, a benzothiazol-5-yl group, a purin-2-yl group, a purin-6-yl group, a purin-7-yl group, a purin-8-yl group, a quinolin-2-yl group, quinolin-3-yl group, a quinolin-4-yl group, quinolin-5-yl group, a quinolin-6-yl group, a quinolin-7-yl group, a quinolin-8-yl group, a 5,6,7,8-tetrahydroquinolin-2-yl group, a 5,6,7,8-tetrahydroquinolin-3-yl group, a 5,6,7,8-tetrahydroquinolin-4-yl group, an isoquinolin-1-yl group, an isoquinolin-3-yl group, an isoquinolin-4-yl group, an isoquinolin-5-yl group, an isoquinolin-6-yl group, an isoquinolin-7-yl group, an quinolin-8-yl group, a quinazolin-4-yl group, a quinoxalin-2-yl group, quinoxalin-5-yl group, and a quinoxalin-6-yl group. A 1H-imidazol-1-yl group, a pyrazol-4-yl group, a thiophen-3-yl group, a furan-2-yl group, a pyridin-3-yl group, a pyridin-4-yl group, an indol-5-yl group, a 1H-pyrrolo[2,3-b]pyridin-5-yl group, a benzofuran-2-yl group, a quinolin-3-yl group, and 5,6,7,8-tetrahydroquinolin-3-yl group are preferable, a 1H-imidazol-1-yl group, a pyridin-3-yl group, a pyridin-4-yl group, an indol-5-yl group, a 1H-pyrrolo[2,3-b]pyridin-5-yl group, a benzofuran-2-yl group, a quinolin-3-yl group, and a 5,6,7,8-tetrahydroquinolin-3-yl group are more preferable, and a 1H-imidazol-1-yl group, a pyridin-3-yl group, and a quinolin-3-yl group are particularly preferable.

In Formula (I), examples of the "substituent(s)" in the unsaturated heterocyclic group represented by $R^1$ include the substituents described above. The substituents) are preferably 1 to 3 of substituent selected from the group consisting of an alkyl group, an alkoxy group, an alkoxy-alkyl group, an aralkyl group, an aralkyloxy-alkyl group, a halogen atom, a halogenoalkyl group, an acyl group, an optionally substituted saturated or unsaturated heterocyclic group, and an optionally substituted aromatic hydrocarbon group, and more preferably 1 to 3 of substituent selected from the group consisting of an alkyl group; an alkoxy group; an unsaturated heterocyclic group optionally having an alkyl group, a halogenoalkyl group, an aralkyl group, or a hydroxyalkyl group; and an aromatic hydrocarbon group optionally having an alkyl group, an alkoxy group, or a carbamoyl group. Herein, examples of the unsaturated heterocyclic group which may be substituted on the unsaturated heterocyclic ring represented by $R^1$ include pyrazol, imidazol, pyridine, pyridine, furan, and thiophene. In addition, examples of the aromatic hydrocarbon group include phenyl and naphthyl.

Specific examples of the "substituent(s)" in the unsaturated heterocyclic group represented by $R^1$ can include a methyl group, an ethyl group, an n-propyl group, an isopropyl group, an n-butyl group, an isobutyl group, a sec-butyl group, a tert-butyl group, a methoxy group, an ethoxy group, an n-propoxy group, an isopropoxy group, a 1-methyl-propoxy group, an n-butoxy group, an isobutoxy group, a tert-butoxy group, a 1H-pyrazol-4-yl group, a 1-methyl-1H-pyrazol-4-yl group, a 1-ethyl-1H-pyrazol-4-yl group, a 1-isopropyl-1H-pyrazol-4-yl group, a 1-benzyl-1H-pyrazol-4-yl group, a 1-(difluoromethyl)-1H-pyrazol-4-yl group, a 1-(hydroxyethyl)-1H-pyrazol-4-yl group, a 1H-imidazol-1-yl group, a pyridin-3-yl group, a pyridin-4-yl group, pyrimidin-5-yl group, a furan-2-yl group, a furan-3-yl group, a thiophen-3-yl group, a phenyl group, a 4-methoxyphenyl group, a 4-carbamoylphenyl group, a isopropylcarbamoyl-phenyl group, and a 4-dimethylcarbamoylphenyl group.

Specific examples of preferable $R^1$ include a 1H-imidazol-1-yl group, a 4-phenyl-1H-imidazol-1-yl group, a 4-(4-carbamoylphenyl)-1H-imidazol-1-yl group, a 4-(4-methoxyphenyl)-1H-imidazol-1-yl group, a 4-(thiophene-3-yl)-1H-imidazol-1-yl group, a 4-(pyridin-3-yl)-1H-imidazol-1-yl group, a 4-(pyridin-4-yl)-1H-imidazol-1-yl group, a 5-methyl-4-(pyridin-3-yl)-1H-imidazol-1-yl group, a 4-(pyrimidin-5-yl)-1H-imidazol-1-yl group, a 4-(furan-2-yl)-1H-imidazol-1-yl group, a 4-(furan-3-yl)-1H-imidazol-1-yl group, a 4-(1H-pyrazol-4-yl)-1H-imidazol-1-yl group, a 4-(1-methyl-1H-pyrazol-4-yl)-1H-imidazol-1-yl group, a 4-(1-ethyl-1H-pyrazol-4-yl)-1H-imidazol-1-yl group, a 4-(1-isopropyl-1H-pyrazol-4-yl)-1H-imidazol-1-yl group, a 4-(1-hydroxymethyl)-(1H-pyrazol-4-yl)-1H-imidazol-1-yl group, a 4-(1-(difluoromethyl)-1H-pyrazol-4-yl)-1H-imidazol-1-yl group, a 4-(1-(hydroxyethyl)-1H-pyrazol-4-yl)-1H-imidazol-1-yl group, a 4-(1-(hydroxymethyl)-1H-pyrazol-4-yl)-1H-imidazol-1-yl group, a 4-(1-benzyl-1H-pyrazol-4-yl)-1H-imidazol-1-yl group, a 4-(1-(benzyloxyethyl)-1H-pyrazol-4-yl)-1H-imidazol-1-yl group, a 1'H-1,4'-biimidazol-1'-yl group, a pyridin-3-yl group, a pyridin-4-yl group, a 5-methoxypyridin-3-yl group, a 6-methoxypyridin-3-yl group, a 1-benzyl-1H-pyrazol-4-yl group, a 1-methyl-1H-indol-5-yl group, a 1H-pyrrolo[2,3-b]pyridin-5-yl group, a 1-methyl-1H-pyrrolo[2,3-b]pyridin-5-yl group, a 1-methoxymethyl-1H-pyrrolo[2,3-b]pyridin-5-yl group, a 5,6,7,8-tetrahydroquinolin-3-yl group, a quinolin-3-yl group, a thiophen-3-yl group, a furan-2-yl group, and a benzofuran-2-yl group. $R^1$ is more preferably a 1H-imidazol-1-yl group, a 4-(pyridin-3-yl)-1H-imidazol-1-yl group, a 4-(pyridin-4-yl)-1H-imidazol-1-yl group, a 4-(1H-pyrazol-4-yl)-1H-imidazol-1-yl group, a 4-(1-methyl-1H-pyrazol-4-yl)-1H-imidazol-1-yl group, a 4-(1-ethyl-1H-pyrazol-4-yl)-1H-imidazol-1-yl group, a 4-(1-isopropyl-1H-pyrazol-4-yl)-1H-imidazol-1-yl group, a 4-(1-benzyl-1H-pyrazol-4-yl)-1H-imidazol-1-yl group, a quinolin-3-yl group, and a 4-(1H-pyrazol-4-yl)-1H-imidazol-1-yl group, and particularly preferably a 4-(1-methyl-1H-pyrazol-4-yl)-1H-imidazol-1-yl group, a 4-(pyridin-3-yl)-1H-imidazol-1-yl group, and a quinolin-3-yl group.

In Formula (I), the "alkyl group having 1 to 6 of carbon atom" in the "optionally substituted alkyl group having 1 to 6 of carbon atom" represented by $R^2$ refers to a linear or branched alkyl group having 1 to 6 of carbon atom, for example, a methyl group, an ethyl group, an n-propyl group, an isopropyl group, an n-butyl group, an isobutyl group, a sec-butyl group, a tert-butyl group, a pentyl group, or a hexyl group, and is preferably a methyl group, an ethyl group, an n-propyl group, or an isopropyl group.

Examples of the "substituent(s)" in the "optionally substituted alkyl group having 1 to 6 of carbon atom" represented by $R^2$ include the substituents described above. Among these, the substituent(s) are preferably a halogen atom.

The halogen atom-substituted alkyl group is preferably a halogenoalkyl group having 1 to 6 of carbon atom, and more preferably a trifluoromethyl group.

The "alkenyl group having 2 to 6 of carbon atom" represented by $R^2$ refers to the alkenyl group having 2 to 6 of carbon atom described above, and is preferably a vinyl group. Examples of the substituent(s) in the alkenyl group include the substituents described above.

$R^2$ is more preferably an optionally substituted alkyl group having 1 to 6 of carbon atom or an optionally substituted alkenyl group having 2 to 6 of carbon atom, even more preferably an alkyl group having 1 to 6 of carbon atom which optionally has a halogen atom, or an alkenyl group having 2 to 6 of carbon atom, and particularly preferably an alkyl group having 1 to 4 of carbon atom which optionally has a halogen atom.

Any one or two of $Y^1$, $Y^2$, $Y^3$, and $Y^4$ are C—$R^4$, and the others are the same or different and represent CH or N. Among these, preferably, any one or two of $Y^1$, $Y^2$, $Y^3$, and $Y^4$ are C—$R^4$, and the others are CH. More preferably, $Y^1$ and $Y^3$ are CH, any one or two of $Y^2$ and $Y^4$ are C—$R^4$, and the others are CH. These preferable aspects are represented by the following formulae:

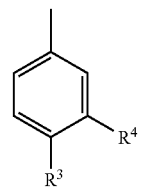

(b1)

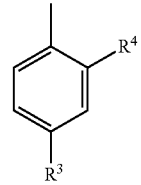

(b2)

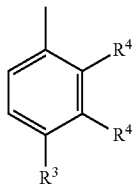
(b3)

the formula, $R^3$ and $R^4$ are as defined above.

Among these, (b1) and (b2) are particularly preferable.

In Formula (I), $R^3$ represents a cyano group or —CO—$R^5$. Among these, —CO—$R^5$ is particularly preferable In Formula (I), $R^4$(s) are the same or different and represent a hydrogen atom, a halogen atom, a cyano group, an optionally substituted alkyl group having 1 to 6 of carbon atom, a cycloalkyl group having 3 to 7 of carbon atom, an alkenyl group having 2 to 6 of carbon atom, an alkoxy group having 1 to 6 of carbon atom, an aromatic hydrocarbon group, —N($R^6$)($R^7$), —S$R^8$, or —CO—$R^9$. Among these, $R^4$ is preferably a halogen atom, an alkyl group having 1 to 6 of carbon atom which optionally has a mono- or di-(C1-C6 alkyl)amino group or a monocyclic 5- to 7-membered saturated heterocyclic group having one or two of any heteroatom of N, S, and O, an alkoxy group having 1 to 6 of carbon atom, —N($R^6$)($R^7$), —S$R^8$, or —CO—$R^9$, and more preferably a halogen atom, an alkyl group having 1 to 6 of carbon atom, or —N($R^6$)($R^7$).

In Formula (I), the "halogen atom" represented by $R^4$ refers to the halogen atom described above and is preferably a chlorine atom.

In Formula (I), the "alkyl group having 1 to 6 of carbon atom" in the "optionally substituted alkyl group having 1 to 6 of carbon atom" represented by $R^4$ refers to the alkyl group having 1 to 6 of carbon atom described above and is preferably a methyl group, an ethyl group, an n-propyl group, or an isopropyl group. Examples of the "substituent(s)" in the "optionally substituted alkyl group having 1 to 6 of carbon atom" represented by $R^4$ include the substituents described above. The "substituent(s)" are preferably mono- or di-(C1-C6 alkyl)amino groups such as an ethylamino group and a dimethylamino group or monocyclic 5- to 7-membered saturated heterocyclic groups having one or two of any heteroatom of N, S, and O such as a pyrrolidyl group and morpholino group.

In Formula (I), the "cycloalkyl group having 3 to 7 of carbon atom" represented by $R^4$ refers to the cycloalkyl group having 3 to 7 of carbon atom described above and is preferably a cyclopropyl group.

In Formula (I), the "alkenyl group having 2 to 6 of carbon atom" represented by $R^4$ refers to the alkenyl group having 2 to 6 of carbon atom and is preferably a vinyl group or a prop-1-en-2-yl group.

In Formula (I), the "alkoxy group having 1 to 6 of carbon atom" represented by $R^4$ refers to the alkoxy group having 1 to 6 of carbon atom described above and is preferably a methoxy group.

In Formula (I), the "mono- or di-alkylamino group" in the "optionally substituted mono- or di-alkylamino group" represented by $R^5$ refers to the mono- or dialkylamino group described above, and is preferably a mono- or di-(C1-C6 alkyl)amino group. Examples of the "substituent(s)" in the "optionally substituted mono- or di-alkylamino group" represented by $R^5$ include the substituents described above.

$R^5$ is more preferably an amino group, a hydroxylamino group, or a mono- or di-(C1-C6 alkyl)amino group, and particularly preferably an amino group.

In Formula (I), the "alkyl group having 1 to 6 of carbon atom" in the "optionally substituted alkyl group having 1 to 6 of carbon atom" represented by $R^6$ or $R^7$ refers to the alkyl group having 1 to 6 of carbon atom described above, and is preferably an ethyl group, an n-propyl group, an n-butyl group, an isobutyl group, a sec-butyl group, or a pentyl group. Examples of the "substituent(s)" in the "optionally substituted alkyl group having 1 to 6 of carbon atom" represented by $R^6$ or $R^7$ include the substituents described above. The "substituent(s)" are preferably a hydroxyl group, cycloalkyl groups having 3 to 7 of carbon atom (for example, a cyclohexyl group), saturated heterocyclic groups (for example, a pyrrolidyl group and a morpholine group), unsaturated heterocyclic groups (for example, a pyridyl group), mono- or di-(C1-C6 alkyl)amino groups (for example, an ethylamino group and a dimethylamino group), (C1-C6 alkyl)thio groups (for example, a methylthio group), or alkoxy groups having 1 to 6 of carbon atom which optionally has a hydroxyl group.

In Formula (I), the "halogenoalkyl group having 1 to 6 of carbon atom" represented by $R^6$ or $R^7$ refers to the halogenoalkyl group having 1 to 6 of carbon atom described above, and is preferably a 2,2-difluoroethyl group or a 2,2,2-trifluoroethyl group.

In Formula (I), examples of the "cycloalkyl group having 3 to 7 of carbon atom" in the "optionally substituted cycloalkyl group having 3 to 7 of carbon atom" represented by $R^6$ or $R^7$ include a cyclopropyl group, cyclobutyl group, a cyclopentyl group, a cyclohexyl group, and a cycloheptyl group, and cycloalkyl group having 3 to 7 of carbon atom is preferably a cyclopropyl group, a cyclopentyl group, or a cyclohexyl group. Examples of the "substituent(s)" in the "optionally substituted cycloalkyl group having 3 to 7 of carbon atom" represented by $R^6$ or $R^7$ include the substituents described above. The substituents) are preferably a hydroxyl group, an amino group, an amino acid-derived acyloxy group, an alkanoylamino group, or an alkylsulfonylamino group.

In Formula (I), the "aralkyl group" in the "optionally substituted aralkyl group" represented by $R^6$ or $R^7$ refers to the aralkyl group described above, and is preferably an aralkyl group having 7 to 12 of carbon atom, specifically, a benzyl group. Examples of the "substituent(s)" in the "optionally substituted aralkyl group" represented by $R^6$ or $R^7$ include the substituents described above. Specific examples of the substituent(s) include saturated heterocyclic groups such as a pyrrolidinyl group.

In Formula (I), the "aromatic hydrocarbon group" in the "optionally substituted aromatic hydrocarbon group" represented by $R^6$ or $R^7$ refers to the aromatic hydrocarbon group having 6 to 14 of carbon atom described above, and is preferably a phenyl group. Examples of the "substituent(s)" in the "optionally substituted aromatic hydrocarbon group" represented by $R^6$ or $R^7$ include the substituents described above. The substituent(s) are preferably halogen atoms, alkylthio groups (for example, a methylthio group), saturated heterocyclic groups (for example, a morpholino group), or substituted carbamoyl groups (for example, a pyrrolidine-carbonyl group).

In the Formula (I), the "saturated heterocyclic group" in the "optionally substituted saturated heterocyclic group" represented by $R^6$ or $R^7$ refers to the saturated heterocyclic group described above, and is preferably a piperidinyl group or a tetrahydropyranyl group. Examples of the "substituent(s)" in the "optionally substituted unsaturated heterocyclic group" represented by $R^6$ or $R^7$ include the substituents described above. The substituent(s) are preferably alkyl groups having 1 to 6 of carbon atom (for example, a methyl group), acyl groups (for example, an acetyl group), carbonyl groups having a saturated heterocyclic group (for example, a 2,6-dihydroxypyrimidinyl-4-carbonyl group), or aminoalkylcarbonyl groups (for example, a 2-aminoacetyl group).

In Formula (I), the "unsaturated heterocyclic group" in the "optionally substituted unsaturated heterocyclic group" represented by $R^6$ or $R^7$ refers to the unsaturated heterocyclic group described above, and is preferably a pyridyl group or an oxazolyl group. Examples of the "substituent(s)" in the "optionally substituted unsaturated heterocyclic group" represented by $R^6$ or $R^7$ include the substituents described above.

In Formula (I), the "saturated heterocyclic group" which is optionally formed by $R^6$ and $R^7$ together with the nitrogen atom to which they are bonded refers to a mono- or bi-cyclic saturated heterocyclic group preferably having 1 to 4 of any atom of an oxygen atom, a nitrogen atom, and a sulfur atom, and for example, a pyrrolidinyl group, piperidinyl group, a piperazinyl group, a hexamethyleneimino group, a morpholino group, a thiomorpholino group, a homopiperazinyl group, a tetrahydrofuranyl group, or tetrahydropyranyl group.

In Formula (I), it is preferred for the combination of $R^6$ and $R^7$ that $R^6$ be a hydrogen atom or an optionally substituted alkyl group having 1 to 6 of carbon atom; and $R^7$ represent a hydrogen atom, an optionally substituted alkyl group having 1 to 6 of carbon atom, an optionally substituted cycloalkyl group having 3 to 7 of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or $R^6$ and $R^7$ optionally form a 5- to 7-membered saturated heterocyclic group, together with the nitrogen atom to which they are bonded. More preferably, $R^6$ is a hydrogen atom, and $R^7$ is a hydrogen atom, an optionally substituted alkyl group having 1 to 6 of carbon atom, an optionally substituted cycloalkyl group having 3 to 7 of carbon atom, or an optionally substituted mono- or bi-cyclic saturated heterocyclic group having 1 to 4 of heteroatom selected from the group consisting of N, S, and O. Particularly preferably, $R^6$ is a hydrogen atom, and $R^7$ is an optionally substituted alkyl group having 1 to 6 of carbon atom or an optionally substituted cycloalkyl group having 3 to 7 of carbon atom.

In Formula (I), the "cycloalkyl group having 3 to 7 of carbon atom" in the "optionally substituted cycloalkyl group having 3 to 7 of carbon atom" represented by $R^8$ refers to the cycloalkyl group having 3 to 7 of carbon atom described above, and is preferably a cyclohexyl group. Examples of the "substituent(s)" in the "optionally substituted cycloalkyl group having 3 to 7 of carbon atom" represented by $R^8$ include the substituents described above. The substituent(s) are preferably a hydroxyl group.

In Formula (I), the "aromatic hydrocarbon group" in the "optionally substituted aromatic hydrocarbon group" represented by $R^8$ refers to the aromatic hydrocarbon group having 6 to 14 of carbon atom described above, and is preferably a phenyl group. Examples of the "substituent(s)" in the "optionally substituted aromatic hydrocarbon group" represented by $R^8$ include the substituents described above. The substituent(s) are preferably a hydroxyl group.

$R^8$ preferably an optionally substituted cycloalkyl group having 3 to 7 of carbon atom, or an optionally substituted aromatic hydrocarbon group having 6 to 14 of carbon atom.

In Formula (I), the "mono- or di-alkylamino group" in the "optionally substituted mono- or di-alkylamino group" represented by $R^9$ refers to the mono- or dialkylamino group described above, and is preferably a mono- or di-(C1-C6 alkyl)amino group. Examples of the "substituent(s)" in the "optionally substituted mono- or di-alkylamino group" represented by $R^9$ include the substituents described above.

$R^9$ is preferably a hydrogen atom, a hydroxyl group, an amino group or a mono- or di-(C1-C6 alkyl)amino group, and particularly preferably a hydrogen atom.

The preferred azabicyclo compound of the invention is a compound of Formula (I), in which $X^1$ is CH or N; $X^2$ is N and $X^3$ and $X^4$ are CH; $Y^1$ and $Y^3$ are CH, any one or two of $Y^2$ and $Y^4$ are C—$R^4$, and the other is CH; $R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group; $R^2$ is an alkyl group having 1 to 6 of carbon atom optionally having a halogen atom or an alkenyl group having 2 to 6 of carbon atom; $R^3$ is —CO—$R^5$; $R^4$ is a halogen atom, an alkyl group having 1 to 6 of carbon atom optionally having a mono- or di-(C1-C6 alkylamino group or a monocyclic 5- to 7-membered saturated heterocyclic group having one or two of any heteroatom of N, S, and O, an alkoxy group having 1 to 6 of carbon atom, —N($R^6$)($R^7$), —$SR^8$, or —CO—$R^9$; $R^5$ is an amino group or mono- or di-(C1-C6 alkyl)amino group; a hydrogen atom or an optionally substituted alkyl group having 1 to 6 of carbon atom; $R^7$ is a hydrogen atom, an optionally substituted alkyl group having 1 to 6 of carbon atom, an optionally substituted cycloalkyl group having 3 to 7 of carbon atom, an optionally substituted aralkyl group having 7 to 12 of carbon atom, an optionally substituted aromatic hydrocarbon group having 6 to 14 of carbon atom, an optionally substituted mono- or bi-cyclic saturated heterocyclic group having 1 to 4 of heteroatom selected from the group consisting of N, S, and O, or an optionally substituted mono- or bi-cyclic unsaturated heterocyclic group having 1 to 4 of heteroatom selected from the group consisting of N, S, and O, or $R^6$ and $R^7$ form a 5- to 7-membered saturated heterocyclic group together with a nitrogen atom to which they are bonded; $R^8$ is an optionally substituted cycloalkyl group having 3 to 7 of carbon atom or an optionally substituted aromatic hydrocarbon group having 6 to 14 of carbon atom; and $R^9$ is a hydrogen atom, a hydroxyl group, an amino group, or a mono- or di-(C1-C6 alkyl)amino group.

More specifically, the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide (hereinafter, referred to as Compound 1).

The salt of the azabicyclo compound of the invention is not particularly limited as long as it is a pharmaceutically acceptable salt, and examples thereof include acid addition salts of inorganic acids (for example, hydrochloric acid, hydrobromic acid, hydroiodic acid, sulfuric acid, nitric acid, and phosphoric acid) and organic acids (for example, formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, p-toluenesulfonic acid, and glutamic acid); salts of inorganic bases (for example, sodium, potassium, magnesium, calcium, and aluminum), organic bases (for example, methylamine, ethylamine, meglumine, and ethanolamine), or a basic amino acids (for example, lysine, arginine, and ornithine); and ammonium salts.

Incidentally, the azabicyclo compound of the invention or a salt thereof can be synthesized according to the method described in WO 2011/004610 A, for example.

As described in Examples below, when the azabicyclo compound of the invention or a salt thereof is administered in combination with extremely various ranges of antitumor agents having different action mechanisms, the antitumor effect is synergistically potentiated. The "other antitumor agent" described in the invention is not particularly limited as long as it is a pharmaceutical having antitumor activity, and as the form thereof, any of a low molecular compound, an antibody, and a nucleic acid may be employed. Specific examples of antitumor agents exhibiting the synergic effect with the azabicyclo compound of the invention or a salt thereof include antitumor antibiotic substances such as amrubicin, doxorubicin, doxyl, epirubicin, and mitomycin C; alkylating agents such as cyclophosphamide and nimustine; platinum-based agents such as cisplatin, carboplatin, and oxaliplatin; pyrimidine-based antimetabolite agents such as 5-fluorouracil (5-FU), tegafur/gimeracil/oteracil potassium (TS-1, generic name "tegafur/gimeracil/oteracil potassium compounding agent" (trade name: "TS-1")), tegafur/uracil (UFT, generic name "tegafur/uracil compounding agent" (trade name: "UFT")), capecitabine, doxifluridine, 5-fluoro-2'-deoxyuridine (FdUrd), gemcitabine, and cytarabine; purine-based antimetabolite agents such as fludarabine, bendamustine, cladribine, and nelarabine; folic acid antimetabolite agents such as pemetrexed and methotrexate; plant alkaloid-based antitumor agents such as paclitaxel (for example, TAXOL or ABRAXANE), docetaxel, irinotecan, and etoposide; immunomodulating drugs such as lenalidomide; low molecular weight molecular targeted drugs such as imatinib, gefitinib, dasatinib, erlotinib, lapatinib, everolimus, temsirolimus, bortezomib, crizotinib, vemurafenib, and ZD6244; and antibody molecular targeted drugs such as bevacizumab, trastuzumab, cetuximab, and rituximab. Among these, in terms of the synergic effect of antitumor effect in the case of concurrently using the azabicyclo compound of the invention or a salt thereof, one or more of agent selected from the group consisting of antitumor antibiotic substances, platinum-based agents, pyrimidine-based antimetabolite agents, purine-based antimetabolite agents, folic acid antimetabolite agents, plant alkaloid-based antitumor agents, immunomodulating drugs, and low molecular weight molecular targeted drugs are preferable.

As a specific antitumor agent, in terms of the synergic effect of antitumor effect in the case of concurrently using the azabicyclo compound of the invention or a salt thereof, one or more of kind(s) selected from the group consisting of amrubicin, doxorubicin, mitomycin C, cisplatin, oxaliplatin, 5-FU, TS-1, UFT, gemcitabine, cytarabine, pemetrexed, paclitaxel (for example, TAXOL or ABRAXANE), docetaxel, irinotecan, etoposide, lenalidomide, imatinib, gefitinib, dasatinib, erlotinib, lapatinib, bortezomib, crizotinib, vemurafenib, and ZD6244 are preferable, one or more of kind(s) selected from the group consisting of amrubicin, doxorubicin, cisplatin, oxaliplatin, gemcitabine, cytarabine, pemetrexed, paclitaxel (for example, TAXOL or ABRAXANE), docetaxel, etoposide, lenalidomide, imatinib, gefitinib, dasatinib, erlotinib, lapatinib, and crizotinib are more preferable, and one or more of kind(s) selected from the group consisting of amrubicin, cisplatin, etoposide, gemcitabine, paclitaxel (for example, TAXOL or ABRAXANE), docetaxel, and crizotinib are particularly preferable.

Specific examples of a cancer to be treated by the antitumor agent of the invention include head and neck cancer, digestive organ cancer (for example, esophageal cancer, stomach cancer, duodenal cancer, liver cancer, biliary tract cancer (for example, gallbladder/bile duct cancer), pancreatic cancer, small intestinal cancer, large intestine cancer (for example, colorectal cancer, colon cancer, or rectal cancer), lung cancer (for example, non-small cell lung cancer or small cell lung cancer), breast cancer, ovarian cancer, uterus cancer (for example, cervical cancer or uterine corpus cancer), kidney cancer, bladder cancer, prostate cancer, skin cancer (for example, malignant melanoma or epidermal cancer), and blood cancer (for example, multiple myeloma or acute myelocytic leukemia). Among these, in terms of the synergic effect of the antitumor effect when the azabicyclo compound of the invention or a salt thereof is used in combination with the antitumor agent, the cancer is preferably digestive organ cancer, lung cancer, breast cancer, skin cancer, or blood cancer, and more preferably colorectal cancer, lung cancer, breast cancer, gallbladder cancer, pancreatic cancer, stomach cancer, skin cancer, or blood cancer. Incidentally, herein, the cancer includes not only primary tumor but also cancer metastasizing to other organ(s) (for example, liver). In addition, the antitumor agent of the invention may be used for postoperative adjuvant chemotherapy which is performed for prevention of recurrence after a tumor is removed surgically or may be used for preoperative adjuvant chemotherapy which is preliminarily performed for removing surgically a tumor.

There is no particular limitation on the administration form of the antitumor agent of the invention, and appropriate form can be selected in accordance with the therapeutic purpose. Specific examples of the form of the antitumor agent include oral agents (for examples, tablets, coated tablets, powder, granules, capsules, and liquid), injections, suppositories, cataplasms, and ointments.

The administration schedule of the antitumor agent of the invention is appropriately selected in the range in which each active ingredient exerts the antitumor effect, and each active ingredient is administered simultaneously or separately at an interval.

The antitumor agent of the invention may be prepared in such a manner that respective active ingredients are separated into multiple dosage forms or are collectively prepared in one dosage form, on the basis of the administration forms or the administration schedules of the active ingredients. In addition, each drug formulation may be produced and sold in one package suitable for use at each event of combined administration or may be produced and sold in separate packages.

The antitumor agent in the invention can be prepared through a generally known method by use of a pharmacologically acceptable carrier, according to the administration form. Such a carrier can be selected from the group consisting of a variety of carriers generally employed in pharmaceuticals, and examples thereof can include an excipient, a binder, a disintegrant, a lubricant, a diluent, a solubilizing agent, a suspending agent, tonicity agent, a pH-adjusting agent, a buffer, stabilizer, a coloring agent, a flavoring agent, and a deodorant.

The invention also relates to an antitumor effect potentiator containing the azabicyclo compound of the invention or a salt thereof, which is used for potentiating the antitumor effect of other antitumor agent(s) with respect to a cancer patient. The antitumor effect potentiator has the formulation aspect of the antitumor agent described above.

The invention also relates to an antitumor agent containing the azabicyclo compound of the invention or a salt thereof, which is used for treating a cancer patient who has been administered other antitumor agent(s). The antitumor agent has the above-described formulation aspect.

The invention also relates to a kit preparation including directions for use in which the azabicyclo compound of the invention or a salt thereof and administration of the azabicyclo compound of the invention or a salt thereof in combination with other antitumor agent(s) to a cancer patient are described. Herein, the "directions for use" may be directions for use in which the above-described dosage is described. Although it does not matter whether the directions for use are legally bound or not, directions for use in which the above-described dosage is recommended are preferable. Specifically, a package insert or a pamphlet is exemplified. In addition, the kit preparation including directions for use may be a kit preparation in which directions for use are printed on or attached to the package of the kit preparation or a kit preparation in which directions for use are enclosed in the package of the kit preparation together with an antitumor agent.

EXAMPLES

Hereinafter, the invention will be described in more detail by means of Examples and Reference Examples.

Example 1

A combination of Compound 1 and docetaxel exhibits the potentiated antitumor activity with respect to a human tumor cell of nude mouse xenograft model having a non-small cell lung cancer (NSCLC) cell NCI-H2170.

NCI-H2170 (ATCC #CRL-5928) as a human non-small cell lung cancer (NSCLC) cell line was obtained from American Type Culture Collection (ATCC; Manassas, Va., USA). In RPMI-1640 (containing 4.5 g/L of glucose, 10 mM of HEPES, and 1 mM of sodium pyruvate) (Wako Pure Chemical Industries, Ltd.) medium supplemented with 10% fetal bovine serum (FBS), cell lines were cultured. The cells cryopreserved in liquid nitrogen were quickly thawed at 37° C., transferred to a tissue culture flask containing a medium, and allowed to grow in a 5% $CO_2$ incubator at 37° C. The NCI-H2170 cell lines were sub-cultured once to twice a week at a dilution ratio of 1:5 to 1:10. The cells which were grown to 80 to 90% confluence in a 75 $cm^2$ flask were washed with 10 mL of phosphate buffer saline (PBS), and 10 mL of 0.25% trypsin-EDTA was then added thereto, followed by incubation until the cells were separated from the surface of the flask. 10 mL of medium for inactivation of trypsin was added thereto, a cell suspension was collected, and after centrifugal separation, the cell pellet was re-suspended in 10 mL of growth medium and then seeded in a 175 $cm^2$ flask into which 30 mL of medium was put, followed by incubation in a 5% $CO_2$ incubator at 37° C. When the flask reached 80 to 90% confluence, the above-described sub-culturing was repeated until cells sufficient for transplantation into mice were obtained.

Five-week old BALB/cAJcl-nu/nu mice (nude mice) were obtained from CREA Japan, Inc. Animals were housed in 5 or 6 microisolator cages under a 12-hour light/12-hour dark cycle, acclimated at least one week before use, and appropriately fed with a usual feed. The animals at the time of transplantation were six- to eight-week old. In order to transplant NCI-H2170 cells to the nude mice, cells were collected as described above, washed in PBS, and re-suspended at a concentration of $5 \times 10^7$ cell/mL in 50% PBS and 50% Matrigel basement membrane matrix (#356237; BD Biosciences; Bedford, Mass., USA). A $5 \times 10^6$ cell/0.1 mL of cell suspension was transplanted subcutaneously to the right dorsal region of the nude mouse by using a 1 mL tuberculin syringe and a 25 G needle.

Subsequently, the cell was allowed to grow for one to two weeks after transplantation until the tumor volume (TV) reached 100 to 300 $mm^3$. Digimatic Caliper was used in measurement of the tumor diameter, the major axis and the minor axis of the tumor were measured, and TV was calculated by the following formula.

TV ($mm^3$)=(Major axis×minor $axis^2$)/2, units of the major axis and the minor axis: mm Animals having an extremely small or large tumor volume were excluded and the remaining animals were allocated to each group by a stratified randomization allocation method using TV as an index. A relative tumor volume (RTV) was calculated from TV as an endpoint. In addition, a treatment/control (T/C) value (t) that is an RTV ratio of the RTV of the pharmaceutical administered group to the RTV of the control group on the end date of test period was calculated as an evaluation index. RTV and T/C (%) were calculated by the following formula.

$RTV = TV_n/TV_1$

T/C (%)=(Average RTV of each pharmaceutical administered group on test end date)/(Average RTV of control group on test end date)×100

$TV_1$ represents the tumor volume of Day 1.

In order to administer Compound 1, a 0.5% hypromellose aqueous solution was prepared. Hypromellose was weighed in a beaker, and distilled water (Otsuka Pharmaceutical Factory, Inc.) was added thereto in an amount of about 80% of the preparation amount. The mixture was completely dissolved by being stirred overnight using a stirrer at a low-temperature chamber, the resultant solution was transferred to a measuring cylinder, and distilled water was added to dilute to the preparation amount. Compound 1 was weighed in a necessary amount, pulverized with an agate mortar, suspended with a 0.5% hypromellose aqueous solution to have a predetermined concentration, and then subjected to ultrasonic treatment, thereby obtaining a homogeneous suspension. 10 mL of this suspension was administered orally per kg of body weight. Incidentally, the suspension was stored in a refrigerator at times other than administration. This suspension is refrigerator-stable for two weeks.

As docetaxel, 80 mg of Taxotere (registered trademark) for intravenous drip infusion (Sanofi-Aventis SA) was dissolved according to the package insert, and was diluted with physiological saline so as to have a predetermined concentration immediately before administration. On the first day of administration, 5 mL of the prepared docetaxel was administered intravenously per kg of body weight.

Both the treatment with 5 mg/kg of body weight of Compound 1 and the treatment with 15 mg/kg of body weight of docetaxel slightly inhibited the growth of NCI-H2170 tumor in the nude mice, and the T/C values were 72 and 86, respectively. In contrast, the concomitant treatment with a combination of 5 mg/kg of body weight of Compound 1 and 15 mg/kg of body weight of docetaxel further inhibited the growth of NCI-H2170 tumor in the nude mice, and the T/C value was 43. Further, the treatment with one of 10 mg/kg of body weight of Compound 1 and 30 mg/kg of body weight of docetaxel or a combination thereof were carried out. However, the effect observed in each concomitant treatment group was potentiated more significantly (P<0.05; Intersection-Union test) compared to the effect observed in the group treated only with any one of pharmaceuticals. The results thereof are shown in FIG. 1. Regarding the average body weight change on the end date of test period, all of the groups treated with the combination of Compound 1 and docetaxel were accompanied with no toxicity with respect to the control group.

Example 2

A combination of Compound 1 and paclitaxel exhibits the potentiated antitumor activity with respect to a human tumor cell of nude mouse xenograft model having NSCLC NCI-H441 cells.

An NCI-H441 cell (ATCC #HTB-174) was transplanted to nude mice according to the description in Example 1. The cell was allowed to grow for one week after transplantation until the large majority of tumors reached 100 to 300 mm$^3$.

In order to administer paclitaxel, paclitaxel was weighed in a necessary amount, ethanol (NACALAI TESQUE, INC.) was added thereto in an amount of 10% of the preparation amount, and the mixture was dissolved by ultrasonic treatment. Next, Cremophor EL (NACALAI TESQUE, INC.) was added thereto in the same amount as ethanol, and the mixture was dissolved by ultrasonic treatment. Physiological saline was added and mixed in an amount of 10% of the preparation amount immediately before administration, thereby preparing a paclitaxel administration solution. On the first day of administration, 5 mL of the paclitaxel administration solution was administered intravenously per kg of body weight.

Figure 2:
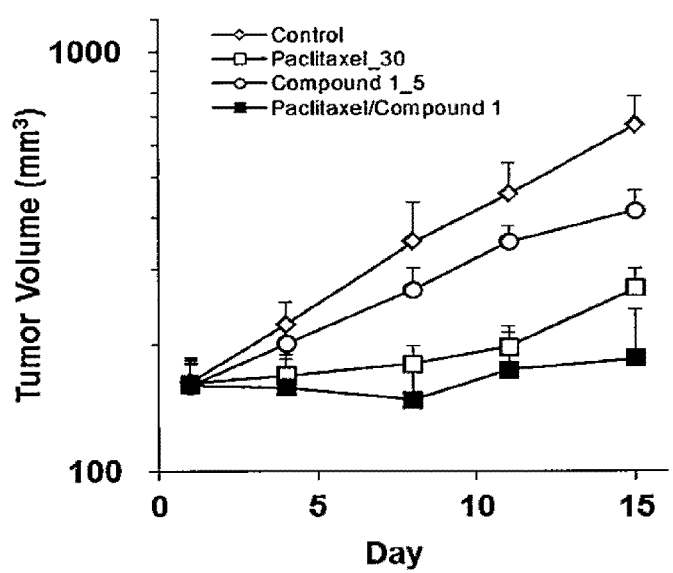
FIG. 2 shows an effect of the combination of Compound 1 and paclitaxel with respect to the rate of tumor growth of a human non-small cell lung cancer line NCI-H441.

As shown in FIG. 2, both the treatment with 5 mg/kg of body weight of Compound 1 and the treatment with 30 mg/kg of body weight of paclitaxel inhibited the growth of NCI-H441 tumor in the nude mice, and the T/C values were 63 and 41, respectively. In contrast, in the case of concomitant treatment with these pharmaceuticals, the inhibitory effect of NCI-H441 tumor growth in the nude mice was potentiated and the T/C value was 28. Further, the treatment with 15 mg/kg of body weight or 60 mg/kg of body weight of docetaxel alone and the concomitant treatment with docetaxel and 5 mg/kg of body weight of Compound 1 were carried out. However, the effect observed in each concomitant treatment group was potentiated more significantly (P<0.05; Intersection-Union test) compared to the effect observed in the group treated only with any one of pharmaceuticals. Regarding the toxicity using the body weight change on the end date of test period as an index, the group treated with the combination of Compound 1 and paclitaxel was well in the tolerable range with respect to the control group. In addition, the same result was also obtained in the stomach cancer line.

Example 3

A combination of Compound 1 and cisplatin exhibits the potentiated antitumor activity with respect to a human tumor cell of nude mouse xenograft model having a stomach cancer line NCI-N87 cell.

An NCI-N87 cell (ATCC #CRL-5822) was transplanted to nude mice according to the description in Example 1. The cell was allowed to grow for one week after transplantation until the large majority of tumors reached 100 to 300 mm$^3$.

As cisplatin, 25 mg of Briplatin for injection (Bristol-Myers Squibb Company) was dissolved according to the package insert, and was diluted with physiological saline so as to have a predetermined concentration immediately before administration. On the first day of administration, 14.0 mL of the prepared cisplatin was administered intravenously per kg of body weight.

Figure 3:
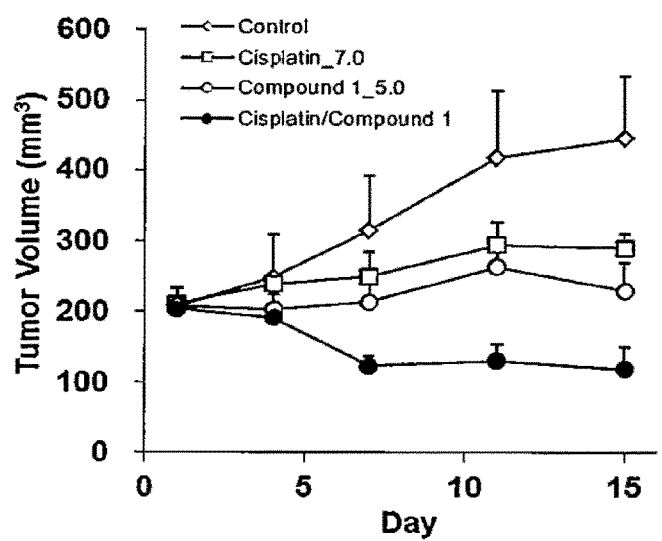
FIG. 3 shows an effect of the combination of Compound 1 and cisplatin with respect to the rate of tumor growth of a human stomach cancer line NCI-N87.

As shown in FIG. 3, both the treatment with 5 mg/kg of body weight of Compound 1 and the treatment with 7 mg/kg of body weight of cisplatin inhibited the growth of NCI-N87 tumor in the nude mice, and the T/C values were 51 and 65, respectively. In contrast, in the case of concomitant treatment with these pharmaceuticals, the inhibitory effect of NCI-N87 tumor growth in the nude mice was potentiated and the T/C value was 26. Further, the treatment with 10 mg/kg of body weight or 20 mg/kg of body weight of Compound 1 alone and the concomitant treatment with Compound 1 and 7 mg/kg of body weight of cisplatin were carried out. However, the effect observed in each concomitant treatment group was potentiated more significantly (P<0.05; Intersection-Union test) compared to the effect observed in the group treated only with any one of pharmaceuticals. Regarding the toxicity using the body weight change on the end date of test period as an index, the group treated with the combination of Compound 1 and cisplatin was well in the tolerable range with respect to the control group.

Example 4

A combination of Compound 1 and amrubicin exhibits the potentiated antitumor activity with respect to a human tumor cell of nude mouse xenograft model having a small cell lung cancer line SBC-1 cell.

An SBC-1 cell (purchased from Health Science Research Resources Bank, #JCRB0816) was transplanted to nude mice according to the description in Example 1. The cell was allowed to grow for one week after transplantation until the large majority of tumors reached 100 to 300 mm$^3$.

As amrubicin, 20 mg of Calsed (registered trademark) for injection (Sumitomo Dainippon Pharma Co., Ltd.) was dissolved according to the package insert, and was diluted with physiological saline so as to have a predetermined concentration immediately before administration. On the first day of administration, 10.0 mL of the prepared amrubicin was administered intravenously per kg of body weight.

On Days 1, 3, 5, 8, 10, and 12, 10.0 mL of Compound 1 was administered orally per kg of body weight.

Figure 4:
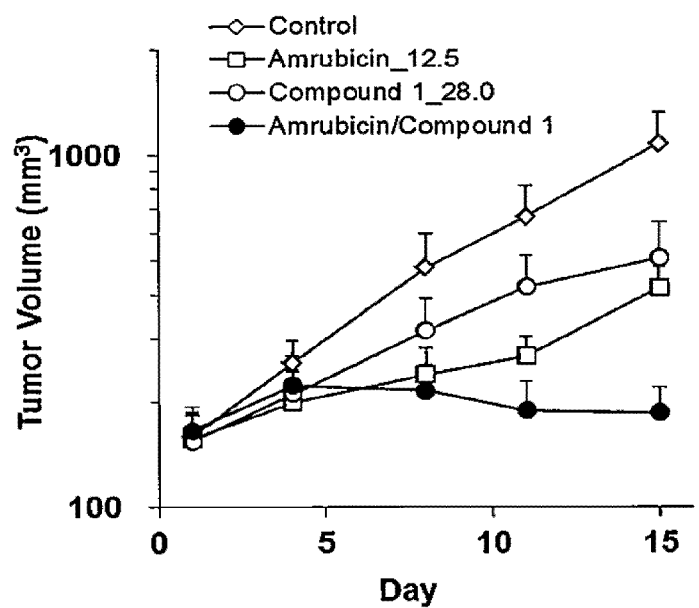
FIG. 4 shows an effect of the combination of Compound 1 and amrubicin with respect to the rate of tumor growth of a human small cell lung cancer cell line SBC-1.

As shown in FIG. 4, both the treatment with 28 mg/kg of body weight of Compound 1 and the treatment with 12.5 mg/kg of body weight of amrubicin inhibited the growth of SBC-1 tumor in the nude mice, and the T/C values were 49 and 40, respectively. In contrast, in the case of concomitant treatment with these pharmaceuticals, the inhibitory effect of SBC-1 tumor growth in the nude mice was potentiated and the T/C value was 17. Further, the treatment with 20 mg/kg of body weight of Compound 1 alone and the concomitant treatment with Compound 1 and 12.5 mg/kg of body weight of amrubicin were carried out. However, the effect observed in each concomitant treatment group was potentiated more significantly (P<0.05; Intersection-Union test) compared to the effect observed in the group treated only with any one of pharmaceuticals. Regarding the toxicity using the body weight change on the end date of test period as an index, the group treated with the combination of Compound 1 and amrubicin was well in the tolerable range with respect to the control group.

Example 5: In Vitro Combination Analysis of Compound 1 and Crizotinib

A. Material and Method

In RPMI-1640 medium (Wako Pure Chemical Industries, Ltd.) supplemented with 10% fetal bovine serum (Thermo Scientific), human stomach cancer cell lines NUGC-4 and MKN45 (Health Science Research Resources Bank, HSRRB) were allowed to grow. All of the cells were maintained at 37° C. and 5% $CO_2$, and sub-cultured once to twice a week at a dilution ratio of 1:5 to 1:20.

Cell Survival Assay

The cell survival rate was measured using CellTiter-Glo. The cells were recovered by a general method, suspended in RPMI-1640 medium supplemented with 10% fetal bovine serum and antibiotic substances (penicillin and streptomycin), and seeded in a 384-well plate. The number of cells to be seeded was set to 500 cell/20 μL per well. The seeded cells were incubated at 37° C. and 5% $CO_2$ for 24 hours, and then 5 μL of a medium supplemented with crizotinib and Compound 1 or Vehicle (DMSO) was added thereto. As crizotinib, nine of a 3-fold dilution series from 10 μM and zero concentration (DMSO) were used, and as Compound 1, seven of 3-fold dilution series from 10 μM and zero concentration (DMSO) were used. All of 80 combinations thereof were examined. With respect to each combination, four wells were allocated. Further, incubation was carried out at 37° C. and 5% $CO_2$ for 72 hours. 25 μL of CellTiter-Glo liquid per well was added, and then incubation was carried out at room temperature for 10 minutes. The chemiluminescence was measured by Envision as a plate reader. The average value of four wells of each combination was calculated from the obtained data, and the standardized cell survival rate was calculated with respect to the control added with a medium supplemented with Vehicle. The Fa (Fraction of Affect) was calculated by subtracting the cell survival rate from 1.

The half inhibition concentration (IC50) of each pharmaceutical was determined using median effect analysis software CalcuSyn 2.0 (CalcuSyn, Inc.). Subsequently, the combination index (CI) of each combination concentration of pharmaceuticals was determined. The CI values of more than 1, equal to 1, and less than 1 each indicate antagonistic effect, additive effect, and synergic effect (Table 1) (Pharmacol Rev. 2006; 58(3):621-81, EMC Complement Altern Med. 2013; 13:212, Anticancer Res. 2005; 25(3B):1909-17).

TABLE 1

(Explanation of combination index value)

| Range of CI (upper limit) | Explanation |
| --- | --- |
| 0.1 | Extremely strong synergic effect |
| 0.3 | Strong synergic effect |
| 0.7 | Synergic effect |
| 0.85 | Moderate synergic effect |
| 0.9 | Slight synergic effect |
| 1 | Substantially additive |
| 1.2 | Modest antagonistic effect |
| 1.45 | Moderate antagonistic effect |
| 3.3 | Antagonistic effect |
| 10 | Strong antagonistic effect |
| >10 | Extremely strong antagonistic effect |

Further, the Fa value close to 1 is considered to be a concentration range in which the effect of one of pharmaceuticals is too strong, and the Fa value close to 0 is considered to be a concentration range in which the effect of one of pharmaceuticals is too weak. These values are not suitable for discussion on the synergistic effect. Therefore, the concentration combination of both the pharmaceuticals satisfying 0.2≤Fa≤0.8 was extracted from the Fa values calculated by 80 concentration combinations of Compound 1 and crizotinib in total in the NUGC-4 cell, and the extracted concentration combination is used in the linear curve fitting by CalcuSyn to obtain a CI.

B. Result

The obtained CI and the concentrations of both pharmaceuticals applied therewith were examined and the concentration range of each of both the pharmaceuticals in which the CI became moderate degree or higher synergic effect (less than 0.85) was found (Table 2).

TABLE 2

| Compound 1 (nM) | Crizotinib (nM) | Pa | CI | | Concomitant ratio |
| --- | --- | --- | --- | --- | --- |
| 13.7174 | 4.57247 | 0.34 | 0.291 | Strong synergic effect | 1:0.33333 |
| 13.7174 | 13.7174 | 0.527 | 0.139 | Strong synergic effect | 1:1 |
| 13.7174 | 41.1523 | 0.53 | 0.383 | Synergic effect | 1:3.00001 |
| 41.1523 | 4.57247 | 0.339 | 0.368 | Synergic effect | 1:0.11111 |
| 41.1523 | 13.7174 | 0.579 | 0.103 | Strong synergic effect | 1:0.33333 |
| 41.1523 | 41.1523 | 0.534 | 0.391 | Synergic effect | 1:1 |
| 41.1523 | 123.457 | 0.567 | 0.816 | Moderate synergic effect | 1:3 |
| 123.457 | 1.52416 | 0.289 | 0.622 | Synergic effect | 1:0.01235 |
| 123.457 | 4.57247 | 0.417 | 0.319 | Synergic effect | 1:0.03704 |
| 123.457 | 13.7174 | 0.581 | 0.149 | Strong synergic effect | 1:0.11111 |
| 123.457 | 41.1523 | 0.582 | 0.3 | Synergic effect | 1:0.33333 |
| 370.37 | 1.52416 | 0.645 | 0.148 | Strong synergic effect | 1:0.00412 |
| 370.37 | 4.57247 | 0.624 | 0.182 | Strong synergic effect | 1:0.01235 |
| 370.37 | 13.7174 | 0.631 | 0.205 | Strong synergic effect | 1:0.03704 |

TABLE 2-continued

| Compound 1 (nM) | Crizotinib (nM) | Fa | CI | | Concomitant ratio |
|---|---|---|---|---|---|
| 370.37 | 41.1523 | 0.64 | 0.278 | Strong synergic effect | 1:0.11111 |
| 370.37 | 123.457 | 0.66 | 0.446 | Synergic effect | 1:0.33333 |
| 1111.11 | 1.52416 | 0.75 | 0.201 | Strong synergic effect | 1:0.00137 |
| 1111.11 | 4.57247 | 0.74 | 0.221 | Strong synergic effect | 1:0.00412 |
| 1111.11 | 13.7174 | 0.742 | 0.227 | Strong synergic effect | 1:0.01235 |
| 1111.11 | 41.1523 | 0.739 | 0.262 | Strong synergic effect | 1:0.03704 |
| 1111.11 | 123.457 | 0.722 | 0.41 | Synergic effect | 1:0.11111 |
| 3333.33 | 41.1523 | 0.717 | 0.833 | Moderate synergic effect | 1:0.01235 |

In the concentration range from 13.7174 nM to 1111.11 nM of Compound 1 and the concentration range from 4.57247 nM to 41.1523 nM of crizotinib in the NUGC-4 cell, a large number of combinations exhibiting a strong synergic effect were found. This means that in these concentration ranges, cell death was induced greater than expected from the additive effect of dosage of respective pharmaceuticals.

In addition, similarly to the result of the NUGC-4 cell described above, regarding the MKN45 cell, when the incubation was carried out for 72 hours while Compound 1 and crizotinib were simultaneously added, a large number of combinations exhibiting a strong synergic effect also were found in the concentration range from 13.7174 nM to 370.37 nM of Compound 1 and the concentration range from 13.7174 nM to 123.457 nM of crizotinib (Table 3).

TABLE 3

| Compound 1 (nM) | Crizotinib (nM) | Fa | CI | | Concomitant ratio |
|---|---|---|---|---|---|
| 13.7174 | 41.1523 | 0.796 | 0.048 | Extremely strong synergic effect | 1:3.00001 |
| 13.7174 | 370.37 | 0.795 | 0.418 | Synergic effect | 1:27.00001 |
| 41.1523 | 13.7174 | 0.346 | 0.772 | Moderate synergic effect | 1:0.33333 |
| 41.1523 | 41.1523 | 0.792 | 0.056 | Extremely strong synergic effect | 1:1 |
| 123.457 | 13.7174 | 0.395 | 0.709 | Moderate synergic effect | 1:0.11111 |
| 370.37 | 1.52416 | 0.562 | 0.34 | Synergic effect | 1:0.00412 |
| 370.37 | 4.57247 | 0.562 | 0.367 | Synergic effect | 1:0.01235 |
| 370.37 | 13.7174 | 0.727 | 0.153 | Strong synergic effect | 1:0.03704 |
| 370.37 | 41.1523 | 0.792 | 0.123 | Strong synergic effect | 1:0.11111 |
| 370.37 | 123.457 | 0.796 | 0.21 | Strong synergic effect | 1:0.33333 |
| 370.37 | 370.37 | 0.78 | 0.575 | Synergic effect | 1:1 |
| 1111.11 | 1.52416 | 0.733 | 0.354 | Synergic effect | 1:0.00137 |
| 1111.11 | 4.57247 | 0.74 | 0.344 | Synergic effect | 1:0.00412 |
| 1111.11 | 13.7174 | 0.723 | 0.408 | Synergic effect | 1:0.01235 |
| 1111.11 | 41.1523 | 0.769 | 0.332 | Synergic effect | 1:0.03704 |
| 1111.11 | 123.457 | 0.753 | 0.523 | Synergic effect | 1:0.11111 |
| 3333.33 | 1.52416 | 0.764 | 0.846 | Moderate synergic effect | 1:0.00046 |
| 3333.33 | 4.57247 | 0.77 | 0.813 | Moderate synergic effect | 1:0.00137 |
| 3333.33 | 41.1523 | 0.776 | 0.827 | Moderate synergic effect | 1:0.01235 |

Example 6: In Vitro Combination Analysis of Compound 1 and Other Antitumor Agents The same in vitro combination analysis was also performed on a combination of Compound 1 and other antitumor agents with respect to a cell line other than those described above. All of the antitumor agents presented in Table 4 to Table 39 exhibited moderate degree or higher synergic effect with Compound 1 (CI<0.85). Particularly, in imatinib, etoposide, erlotinib, oxaliplatin, gefitinib, gemcitabine, cisplatin, cytarabine, dasatinib, doxorubicin, docetaxel, paclitaxel, pemetrexed, lapatinib, and lenalidomide, a strong synergic effect (CI<0.30) exhibited in one or more of concentration combination.

TABLE 4

<Antitumor agent: 5-FU, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 5555.56 | 0.563 | 0.475 | Synergic effect | 1:405.00095 |
| 41.1523 | 5555.56 | 0.537 | 0.613 | Synergic effect | 1:134.99999 |
| 3333.33 | 7.62079 | 0.676 | 0.804 | Moderate synergic effect | 1:0.00229 |
| 3333.33 | 22.8624 | 0.678 | 0.797 | Moderate synergic effect | 1:0.00686 |
| 3333.33 | 68.5871 | 0.698 | 0.726 | Moderate synergic effect | 1:0.02058 |
| 3333.33 | 205.761 | 0.688 | 0.765 | Moderate synergic effect | 1:0.06173 |
| 3333.33 | 617.284 | 0.701 | 0.728 | Moderate synergic effect | 1:0.18519 |
| 3333.33 | 1851.85 | 0.716 | 0.698 | Synergic effect | 1:0.55556 |
| 3333.33 | 5555.56 | 0.712 | 0.786 | Moderate synergic effect | 1:1.66667 |

TABLE 5

<Antitumor agent: ZD6244, Cancer type: malignant melanoma, Cell line: A375>

| Compound 1 (nM) | Antitumor agent (nM) | Fa | CI | CI_COMMENT | Concomitant ratio |
|---|---|---|---|---|---|
| 13.7174 | 41.1523 | 0.252 | 0.55 | Synergic effect | 1:3.00001 |
| 13.7174 | 123.457 | 0.479 | 0.314 | Synergic effect | 1:9.00003 |
| 13.7174 | 370.37 | 0.59 | 0.442 | Synergic effect | 1:27.00001 |
| 13.7174 | 1111.11 | 0.68 | 0.692 | Synergic effect | 1:81.00004 |
| 41.1523 | 123.457 | 0.447 | 0.415 | Synergic effect | 1:3 |
| 41.1523 | 370.37 | 0.577 | 0.501 | Synergic effect | 1:8.99998 |
| 41.1523 | 1111.11 | 0.685 | 0.679 | Synergic effect | 1:26.99995 |
| 123.457 | 123.457 | 0.432 | 0.546 | Synergic effect | 1:1 |
| 123.457 | 370.37 | 0.572 | 0.576 | Synergic effect | 1:2.99999 |
| 123.457 | 1111.11 | 0.681 | 0.741 | Moderate synergic effect | 1:8.99998 |
| 370.37 | 41.1523 | 0.352 | 0.758 | Moderate synergic effect | 1:0.11111 |
| 370.37 | 123.457 | 0.443 | 0.772 | Moderate synergic effect | 1:0.33333 |
| 370.37 | 370.37 | 0.606 | 0.624 | Synergic effect | 1:1 |
| 370.37 | 1111.11 | 0.69 | 0.813 | Moderate synergic effect | 1:3 |

TABLE 5-continued

<Antitumor agent: ZD6244, Cancer type: malignant melanoma, Cell line: A375>

| Compound 1 (nM) | Antitumor agent (nM) | Fa | CI | CI_COMMENT | Concomitant ratio |
|---|---|---|---|---|---|
| 1111.11 | 41.1523 | 0.61 | 0.741 | Moderate synergic effect | 1:0.03704 |
| 1111.11 | 123.457 | 0.68 | 0.63 | Synergic effect | 1:0.11111 |
| 1111.11 | 370.37 | 0.753 | 0.547 | Synergic effect | 1:0.33333 |
| 1111.11 | 1111.11 | 0.769 | 0.722 | Moderate synergic effect | 1:1 |

TABLE 6

<Antitumor agent: SN-38, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 13.7174 | 0.564 | 0.437 | Synergic effect | 1:1 |
| 41.1523 | 13.7174 | 0.514 | 0.652 | Synergic effect | 1:0.33333 |
| 41.1523 | 41.1523 | 0.773 | 0.384 | Synergic effect | 1:1 |
| 123.457 | 41.1523 | 0.719 | 0.578 | Synergic effect | 1:0.33333 |
| 3333.33 | 1.52416 | 0.557 | 0.584 | Synergic effect | 1:0.00046 |
| 3333.33 | 4.57247 | 0.558 | 0.694 | Synergic effect | 1:0.00137 |
| 3333.33 | 13.7174 | 0.611 | 0.807 | Moderate synergic effect | 1:0.00412 |
| 3333.33 | 41.1523 | 0.785 | 0.556 | Synergic effect | 1:0.01235 |

TABLE 7

<Antitumor agent: imatinib, Cancer type: acute myelocytic leukemia, Cell line: Kasumi-1>

| Compound 1 (nM) | Antitumor agent (nM) | Fa | CI | CI_COMMENT | Concomitant ratio |
|---|---|---|---|---|---|
| 13.7174 | 370.37 | 0.327 | 0.566 | Synergic effect | 1:27.00001 |
| 13.7174 | 1111.11 | 0.488 | 0.272 | Strong synergic effect | 1:81.00004 |
| 13.7174 | 3333.33 | 0.51 | 0.595 | Synergic effect | 1:243.00013 |
| 41.1523 | 370.37 | 0.369 | 0.446 | Synergic effect | 1:8.99998 |
| 41.1523 | 1111.11 | 0.52 | 0.256 | Strong synergic effect | 1:26.99995 |
| 41.1523 | 3333.33 | 0.55 | 0.443 | Synergic effect | 1:80.99985 |
| 123.457 | 370.37 | 0.409 | 0.561 | Synergic effect | 1:2.99999 |
| 123.457 | 1111.11 | 0.564 | 0.335 | Synergic effect | 1:8.99998 |
| 123.457 | 3333.33 | 0.556 | 0.576 | Synergic effect | 1:26.99993 |
| 370.37 | 4.57247 | 0.616 | 0.592 | Synergic effect | 1:0.01235 |
| 370.37 | 13.7174 | 0.621 | 0.583 | Synergic effect | 1:0.03704 |
| 370.37 | 41.1523 | 0.576 | 0.673 | Synergic effect | 1:0.11111 |
| 370.37 | 123.457 | 0.599 | 0.631 | Synergic effect | 1:0.33333 |
| 370.37 | 370.37 | 0.632 | 0.578 | Synergic effect | 1:1 |
| 370.37 | 1111.11 | 0.694 | 0.48 | Synergic effect | 1:3 |
| 370.37 | 3333.33 | 0.697 | 0.516 | Synergic effect | 1:9 |
| 370.37 | 30000 | 0.737 | 0.722 | Moderate synergic effect | 1:81.00008 |

TABLE 8

<Antitumor agent: etoposide, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 1111.11 | 0.421 | 0.772 | Moderate synergic effect | 1:81.00004 |
| 41.1523 | 3333.33 | 0.638 | 0.741 | Moderate synergic effect | 1:80.99985 |
| 123.457 | 1111.11 | 0.495 | 0.638 | Synergic effect | 1:8.99998 |
| 123.457 | 3333.33 | 0.655 | 0.723 | Moderate synergic effect | 1:26.99993 |
| 370.37 | 3333.33 | 0.71 | 0.648 | Synergic effect | 1:9 |
| 1111.11 | 1.52416 | 0.637 | 0.716 | Moderate synergic effect | 1:0.00137 |
| 1111.11 | 4.57247 | 0.64 | 0.709 | Moderate synergic effect | 1:0.00412 |
| 1111.11 | 13.7174 | 0.623 | 0.754 | Moderate synergic effect | 1:0.01235 |
| 1111.11 | 41.1523 | 0.638 | 0.722 | Moderate synergic effect | 1:0.03704 |
| 1111.11 | 123.457 | 0.671 | 0.655 | Synergic effect | 1:0.11111 |
| 1111.11 | 370.37 | 0.685 | 0.662 | Synergic effect | 1:0.33333 |
| 1111.11 | 1111.11 | 0.714 | 0.689 | Synergic effect | 1:1 |
| 1111.11 | 3333.33 | 0.753 | 0.808 | Moderate synergic effect | 1:3 |

TABLE 9

<Antitumor agent: etoposide, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 3333.33 | 0.279 | 0.29 | Strong synergic effect | 1:243.00013 |
| 13.7174 | 10000 | 0.624 | 0.037 | Extremely strong synergic effect | 1:729.00112 |
| 41.1523 | 10000 | 0.672 | 0.028 | Extremely strong synergic effect | 1:242.99978 |
| 123.457 | 3333.33 | 0.23 | 0.649 | Synergic effect | 1:26.99993 |
| 123.457 | 10000 | 0.616 | 0.061 | Extremely strong synergic effect | 1:80.99986 |
| 370.37 | 10000 | 0.587 | 0.132 | Strong synergic effect | 1:27.00003 |
| 1111.11 | 10000 | 0.472 | 0.555 | Synergic effect | 1:9.00001 |
| 10000 | 3333.33 | 0.782 | 0.79 | Moderate synergic effect | 1:0.33333 |
| 10000 | 10000 | 0.783 | 0.769 | Moderate synergic effect | 1:1 |

TABLE 10

<Antitumor agent: erlotinib, Cancer type: non-small cell lung cancer, Cell line: A549>

| Compound 1 (nM) | Antitumor agent (nM) | Fa | CI | CI_COMMENT | Concomitant ratio |
|---|---|---|---|---|---|
| 13.7174 | 370.37 | 0.275 | 0.572 | Synergic effect | 1:27 |
| 13.7174 | 1111.11 | 0.377 | 0.715 | Moderate synergic effect | 1:81 |
| 13.7174 | 10000 | 0.695 | 0.611 | Synergic effect | 1:729 |
| 41.1523 | 123.457 | 0.275 | 0.36 | Synergic effect | 1:3 |
| 41.1523 | 370.37 | 0.345 | 0.426 | Synergic effect | 1:9 |
| 41.1523 | 1111.11 | 0.366 | 0.749 | Moderate synergic effect | 1:27 |
| 41.1523 | 3333.33 | 0.516 | 0.825 | Moderate synergic effect | 1:81 |
| 41.1523 | 10000 | 0.729 | 0.479 | Synergic effect | 1:243 |
| 123.457 | 123.457 | 0.281 | 0.716 | Moderate synergic effect | 1:1 |

TABLE 10-continued

<Antitumor agent: erlotinib, Cancer type: non-small cell lung cancer, Cell line: A549>

| Compound 1 (nM) | Antitumor agent (nM) | Fa | CI | CI_COMMENT | Concomitant ratio |
|---|---|---|---|---|---|
| 123.457 | 370.37 | 0.359 | 0.653 | Synergic effect | 1:3 |
| 123.457 | 10000 | 0.72 | 0.58 | Synergic effect | 1:81 |
| 370.37 | 1.52416 | 0.558 | 0.554 | Synergic effect | 1:0 |
| 370.37 | 4.57247 | 0.581 | 0.508 | Synergic effect | 1:0.01 |
| 370.37 | 13.7174 | 0.549 | 0.576 | Synergic effect | 1:0.04 |
| 370.37 | 41.1523 | 0.579 | 0.517 | Synergic effect | 1:0.11 |
| 370.37 | 123.457 | 0.683 | 0.344 | Synergic effect | 1:0.33 |
| 370.37 | 370.37 | 0.718 | 0.305 | Synergic effect | 1:1 |
| 370.37 | 1111.11 | 0.772 | 0.253 | Strong synergic effect | 1:3 |
| 1111.11 | 13.7174 | 0.795 | 0.58 | Synergic effect | 1:0.01 |

TABLE 11

<Antitumor agent: oxaliplatin, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 3333.33 | 0.489 | 0.562 | Synergic effect | 1:243.00013 |
| 13.7174 | 10000 | 0.784 | 0.104 | Strong synergic effect | 1:729.00112 |
| 41.1523 | 3333.33 | 0.488 | 0.604 | Synergic effect | 1:80.99985 |
| 41.1523 | 10000 | 0.777 | 0.129 | Strong synergic effect | 1:242.99978 |
| 123.457 | 3333.33 | 0.498 | 0.666 | Synergic effect | 1:26.99993 |
| 123.457 | 10000 | 0.79 | 0.158 | Strong synergic effect | 1:80.99986 |
| 370.37 | 1.52416 | 0.461 | 0.539 | Synergic effect | 1:0.00412 |
| 370.37 | 4.57247 | 0.484 | 0.508 | Synergic effect | 1:0.01235 |
| 370.37 | 13.7174 | 0.463 | 0.538 | Synergic effect | 1:0.03704 |
| 370.37 | 41.1523 | 0.483 | 0.516 | Synergic effect | 1:0.11111 |
| 370.37 | 123.457 | 0.509 | 0.493 | Synergic effect | 1:0.33333 |
| 370.37 | 370.37 | 0.558 | 0.453 | Synergic effect | 1:1 |
| 370.37 | 1111.11 | 0.604 | 0.439 | Synergic effect | 1:3 |
| 370.37 | 3333.33 | 0.771 | 0.261 | Strong synergic effect | 1:9 |

TABLE 12

<Antitumor agent: gefitinib, Cancer type: non-small cell lung cancer, Cell line: HCC827>

| Compound 1 (nM) | Antitumor agent (nM) | Fa | CI | CI_COMMENT | Concomitant ratio |
|---|---|---|---|---|---|
| 13.7174 | 2.28624 | 0.215 | 0.66 | Synergic effect | 1:0.16667 |
| 13.7174 | 6.85871 | 0.477 | 0.262 | Strong synergic effect | 1:0.5 |
| 13.7174 | 20.5761 | 0.739 | 0.125 | Strong synergic effect | 1:1.5 |
| 41.1523 | 6.85871 | 0.442 | 0.382 | Synergic effect | 1:0.16667 |
| 41.1523 | 20.5761 | 0.721 | 0.154 | Strong synergic effect | 1:0.5 |
| 41.1523 | 61.7284 | 0.798 | 0.223 | Strong synergic effect | 1:1.5 |
| 123.457 | 20.5761 | 0.68 | 0.248 | Strong synergic effect | 1:0.16667 |
| 123.457 | 61.7284 | 0.751 | 0.364 | Synergic effect | 1:0.5 |
| 123.457 | 185.185 | 0.797 | 0.676 | Synergic effect | 1:1.5 |
| 370.37 | 20.5761 | 0.598 | 0.63 | Synergic effect | 1:0.05556 |
| 370.37 | 61.7284 | 0.662 | 0.846 | Moderate synergic effect | 1:0.16667 |
| 1111.11 | 0.762079 | 0.75 | 0.321 | Synergic effect | 1:0.00069 |
| 1111.11 | 2.28624 | 0.749 | 0.332 | Synergic effect | 1:0.00206 |

TABLE 12-continued

<Antitumor agent: gefitinib, Cancer type: non-small cell lung cancer, Cell line: HCC827>

| Compound 1 (nM) | Antitumor agent (nM) | Fa | CI | CI_COMMENT | Concomitant ratio |
|---|---|---|---|---|---|
| 1111.11 | 6.85871 | 0.753 | 0.346 | Synergic effect | 1:0.00617 |
| 1111.11 | 20.5761 | 0.776 | 0.345 | Synergic effect | 1:0.01852 |
| 1111.11 | 61.7284 | 0.774 | 0.53 | Synergic effect | 1:0.05556 |
| 3333.33 | 2.28624 | 0.796 | 0.654 | Synergic effect | 1:0.00069 |
| 3333.33 | 6.85871 | 0.787 | 0.726 | Moderate synergic effect | 1:0.00206 |
| 3333.33 | 20.5761 | 0.799 | 0.699 | Synergic effect | 1:0.00617 |

TABLE 13

<Antitumor agent: gemcitabine, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 13.7174 | 0.767 | 0.038 | Extremely strong synergic effect | 1:1 |
| 41.1523 | 13.7174 | 0.697 | 0.111 | Strong synergic effect | 1:0.33333 |
| 123.457 | 13.7174 | 0.736 | 0.103 | Strong synergic effect | 1:0.11111 |
| 370.37 | 13.7174 | 0.598 | 0.585 | Synergic effect | 1:0.03704 |
| 370.37 | 123.457 | 0.75 | 0.528 | Synergic effect | 1:0.33333 |
| 1111.11 | 4.57247 | 0.675 | 0.641 | Synergic effect | 1:0.00412 |
| 1111.11 | 13.7174 | 0.783 | 0.369 | Synergic effect | 1:0.01235 |
| 1111.11 | 41.1523 | 0.773 | 0.455 | Synergic effect | 0.03704 |
| 1111.11 | 123.457 | 0.762 | 0.713 | Moderate synergic effect | 1:0.11111 |

TABLE 14

<Antitumor agent: gemcitabine, Cancer type: gallbladder cancer, Cell line: TGBC2TKB>

| Compound 1 (nM) | Antitumor agent (nM) | Fa | CI | CI_COMMENT | Concomitant ratio |
|---|---|---|---|---|---|
| 500.0 | 62.5 | 0.660 | 0.371 | Synergic effect | 1:0.13 |
| 500.0 | 125.0 | 0.708 | 0.365 | Synergic effect | 1:0.25 |
| 500.0 | 250.0 | 0.721 | 0.450 | Synergic effect | 1:0.5 |
| 500.0 | 500.0 | 0.715 | 0.682 | Synergic effect | 1:1 |
| 1000.0 | 62.5 | 0.652 | 0.686 | Synergic effect | 1:0.06 |
| 1000.0 | 125.0 | 0.695 | 0.649 | Synergic effect | 1:0.13 |
| 1000.0 | 250.0 | 0.700 | 0.756 | Moderate synergic effect | 1:0.25 |

TABLE 15

<Antitumor agent: gemcitabine, Cancer type: non-small cell lung cancer, Cell line: NCI-H522>

| Compound 1 (nM) | Antitumor agent (nM) | Fa | CI | CI_COMMENT | Concomitant ratio |
|---|---|---|---|---|---|
| 1250 | 200 | 0.391 | 0.723 | Moderate synergic effect | 1:0.16 |
| 1250 | 400 | 0.470 | 0.595 | Synergic effect | 1:0.32 |
| 1250 | 800 | 0.567 | 0.490 | Synergic effect | 1:0.64 |
| 2500 | 200 | 0.527 | 0.435 | Synergic effect | 1:0.08 |
| 2500 | 400 | 0.602 | 0.329 | Synergic effect | 1:0.16 |
| 2500 | 800 | 0.594 | 0.502 | Synergic effect | 1:0.32 |
| 5000 | 200 | 0.578 | 0.522 | Synergic effect | 1:0.04 |

TABLE 15-continued

<Antitumor agent: gemcitabine, Cancer type: non-small cell lung cancer, Cell line: NCI-H522>

| Compound 1 (nM) | Antitumor agent (nM) | Fa | CI | CI_COMMENT | Concomitant ratio |
|---|---|---|---|---|---|
| 5000 | 400 | 0.644 | 0.376 | Synergic effect | 1:0.08 |
| 5000 | 800 | 0.627 | 0.548 | Synergic effect | 1:0.16 |
| 10000 | 200 | 0.618 | 0.718 | Moderate synergic effect | 1:0.02 |
| 10000 | 400 | 0.638 | 0.675 | Synergic effect | 1:0.04 |

TABLE 16

<Antitumor agent: gemcitabine, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 123.457 | 0.649 | 0.429 | Synergic effect | 1:9.00003 |
| 41.1523 | 370.37 | 0.8 | 0.469 | Synergic effect | 1:8.99998 |
| 123.457 | 123.457 | 0.59 | 0.62 | Synergic effect | 1:1 |
| 370.37 | 123.457 | 0.566 | 0.767 | Moderate synergic effect | 1:0.33333 |
| 1111.11 | 123.457 | 0.606 | 0.781 | Moderate synergic effect | 1:0.11111 |

TABLE 17

<Antitumor agent: cisplatin, Cancer type: small cell lung cancer, Cell line: NCI-H69>

| Compound 1 (nM) | Antitumor agent (nM) | Fa | CI | CI_COMMENT | Concomitant ratio |
|---|---|---|---|---|---|
| 1000 | 625 | 0.515 | 0.787 | Moderate synergic effect | 1:0.63 |
| 1000 | 5000 | 0.798 | 0.791 | Moderate synergic effect | 1:5 |
| 1000 | 10000 | 0.868 | 0.847 | Moderate synergic effect | 1:10 |
| 2000 | 625 | 0.717 | 0.582 | Synergic effect | 1:0.31 |
| 2000 | 1250 | 0.694 | 0.783 | Moderate synergic effect | 1:0.63 |
| 2000 | 2500 | 0.785 | 0.679 | Synergic effect | 1:1.25 |
| 2000 | 5000 | 0.847 | 0.681 | Synergic effect | 1:2.5 |
| 2000 | 10000 | 0.891 | 0.763 | Moderate synergic effect | 1:5 |

TABLE 18

<Antitumor agent: cisplatin, Cancer type: non-small cell lung cancer, Cell line: A549>

| Compound 1 (nM) | Antitumor agent (nM) | Fa | CI | CI_COMMENT | Concomitant ratio |
|---|---|---|---|---|---|
| 13.7174 | 22.8624 | 0.337 | 0.149 | Strong synergic effect | 1:1.66667 |
| 13.7174 | 68.5871 | 0.321 | 0.193 | Strong synergic effect | 1:5.00001 |
| 13.7174 | 50000 | 0.752 | 0.465 | Synergic effect | 1:3645.00561 |
| 41.1523 | 22.8624 | 0.302 | 0.519 | Synergic effect | 1:0.55556 |
| 41.1523 | 68.5871 | 0.324 | 0.484 | Synergic effect | 1:1.66667 |
| 41.1523 | 50000 | 0.705 | 0.837 | Moderate synergic effect | 1:1214.99892 |
| 123.457 | 22.8624 | 0.507 | 0.516 | Synergic effect | 1:0.18519 |
| 123.457 | 68.5871 | 0.5 | 0.54 | Synergic effect | 1:0.55555 |
| 123.457 | 50000 | 0.763 | 0.517 | Synergic effect | 1:404.99931 |
| 370.37 | 22.8624 | 0.797 | 0.293 | Strong synergic effect | 1:0.06173 |
| 370.37 | 68.5871 | 0.763 | 0.375 | Synergic effect | 1:0.18519 |
| 370.37 | 1851.85 | 0.666 | 0.722 | Moderate synergic effect | 1:5 |
| 370.37 | 16666.7 | 0.751 | 0.558 | Synergic effect | 1:45.00014 |

TABLE 19

<Antitumor agent: cisplatin, Cancer type: epidermal cancer, Cell line: KB>

| Compound 1 (nM) | Antitumor agent (nM) | Fa | CI | CI_COMMENT | Concomitant ratio |
|---|---|---|---|---|---|
| 250 | 313 | 0.743 | 0.816 | Moderate synergic effect | 1:1.25 |
| 250 | 625 | 0.871 | 0.758 | Moderate synergic effect | 1:2.5 |
| 500 | 156 | 0.887 | 0.608 | Synergic effect | 1:0.31 |
| 500 | 313 | 0.932 | 0.546 | Synergic effect | 1:0.63 |
| 500 | 625 | 0.953 | 0.568 | Synergic effect | 1:1.25 |

TABLE 20

<Antitumor agent: cytarabine, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 41.1523 | 0.357 | 0.412 | Synergic effect | 1:3.00001 |
| 13.7174 | 123.457 | 0.574 | 0.346 | Synergic effect | 1:9.00003 |
| 13.7174 | 370.37 | 0.722 | 0.408 | Synergic effect | 1:27.00001 |
| 41.1523 | 41.1523 | 0.369 | 0.447 | Synergic effect | 1:1 |
| 41.1523 | 123.457 | 0.565 | 0.393 | Synergic effect | 1:3 |
| 41.1523 | 370.37 | 0.695 | 0.506 | Synergic effect | 1:8.99998 |

TABLE 20-continued

<Antitumor agent: cytarabine, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 123.457 | 41.1523 | 0.409 | 0.518 | Synergic effect | 1:0.33333 |
| 123.457 | 123.457 | 0.533 | 0.566 | Synergic effect | 1:1 |
| 123.457 | 370.37 | 0.755 | 0.373 | Synergic effect | 1:2.99999 |
| 370.37 | 1.52416 | 0.393 | 0.774 | Moderate synergic effect | 1:0.00412 |
| 370.37 | 13.7174 | 0.416 | 0.778 | Moderate synergic effect | 1:0.03704 |
| 370.37 | 41.1523 | 0.65 | 0.347 | Synergic effect | 1:0.11111 |
| 370.37 | 123.457 | 0.78 | 0.234 | Strong synergic effect | 1:0.33333 |
| 1111.11 | 1.52416 | 0.725 | 0.592 | Synergic effect | 1:0.00137 |
| 1111.11 | 4.57247 | 0.739 | 0.555 | Synergic effect | 1:0.00412 |
| 1111.11 | 13.7174 | 0.698 | 0.687 | Synergic effect | 1:0.01235 |
| 1111.11 | 41.1523 | 0.77 | 0.5 | Synergic effect | 1:0.03704 |

TABLE 21

<Antitumor agent: cytarabine, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 370.37 | 0.557 | 0.831 | Moderate synergic effect | 1:27.00001 |
| 13.7174 | 1111.11 | 0.769 | 0.55 | Synergic effect | 1:81.00004 |
| 41.1523 | 370.37 | 0.56 | 0.82 | Moderate synergic effect | 1:8.99998 |
| 41.1523 | 1111.11 | 0.769 | 0.552 | Synergic effect | 1:26.99995 |
| 123.457 | 1111.11 | 0.74 | 0.712 | Moderate synergic effect | 1:8.99998 |
| 370.37 | 370.37 | 0.594 | 0.706 | Moderate synergic effect | 1:1 |
| 1111.11 | 41.1523 | 0.325 | 0.696 | Synergic effect | 1:0.03704 |
| 3333.33 | 1.52416 | 0.552 | 0.512 | Synergic effect | 1:0.00046 |
| 3333.33 | 4.57247 | 0.527 | 0.55 | Synergic effect | 1:0.00137 |
| 3333.33 | 13.7174 | 0.596 | 0.483 | Synergic effect | 1:0.00412 |
| 3333.33 | 41.1523 | 0.672 | 0.425 | Synergic effect | 1:0.01235 |
| 3333.33 | 123.457 | 0.688 | 0.481 | Synergic effect | 1:0.03704 |
| 3333.33 | 370.37 | 0.711 | 0.636 | Synergic effect | 1:0.11111 |

TABLE 22

<Antitumor agent: dasatinib, Cancer type: acute myelocytic leukemia, Cell line: Kasumi-1>

| Compound 1 (nM) | Antitumor agent (nM) | Fa | CI | CI_COMMENT | Concomitant ratio |
|---|---|---|---|---|---|
| 13.7174 | 13.7174 | 0.527 | 0.265 | Strong synergic effect | 1:1 |
| 13.7174 | 41.1523 | 0.628 | 0.195 | Strong synergic effect | 1:3.00001 |
| 13.7174 | 123.457 | 0.666 | 0.298 | Strong synergic effect | 1:9.00003 |
| 13.7174 | 370.37 | 0.668 | 0.793 | Moderate synergic effect | 1:27.00001 |
| 41.1523 | 13.7174 | 0.534 | 0.385 | Synergic effect | 1:0.33333 |
| 41.1523 | 41.1523 | 0.602 | 0.368 | Synergic effect | 1:1 |
| 41.1523 | 123.457 | 0.648 | 0.462 | Synergic effect | 1:3 |
| 123.457 | 13.7174 | 0.556 | 0.701 | Moderate synergic effect | 1:0.11111 |
| 123.457 | 41.1523 | 0.683 | 0.383 | Synergic effect | 1:0.33333 |
| 123.457 | 123.457 | 0.65 | 0.699 | Synergic effect | 1:1 |
| 123.457 | 370.37 | 0.711 | 0.665 | Synergic effect | 1:2.99999 |
| 370.37 | 41.1523 | 0.779 | 0.57 | Synergic effect | 1:0.11111 |

TABLE 22-continued

<Antitumor agent: dasatinib, Cancer type: acute myelocytic leukemia, Cell line: Kasumi-1>

| Compound 1 (nM) | Antitumor agent (nM) | Fa | CI | CI_COMMENT | Concomitant ratio |
|---|---|---|---|---|---|
| 370.37 | 123.457 | 0.794 | 0.536 | Synergic effect | 1:0.33333 |
| 370.37 | 370.37 | 0.8 | 0.566 | Synergic effect | 1:1 |

TABLE 23

<Antitumor agent: doxorubicin, Cancer type: small cell lung cancer, Cell line: SBC-1>

| Compound 1 (nM) | Antitumor agent (nM) | Fa | CI | CI_COMMENT | Concomitant ratio |
|---|---|---|---|---|---|
| 500.0 | 62.5 | 0.789 | 0.542 | Synergic effect | 1:0.13 |
| 500.0 | 125.0 | 0.886 | 0.509 | Synergic effect | 1:0.25 |
| 1000.0 | 15.6 | 0.647 | 0.584 | Synergic effect | 1:0.02 |
| 1000.0 | 31.3 | 0.826 | 0.300 | Synergic effect | 1:0.03 |
| 1000.0 | 62.5 | 0.906 | 0.244 | Strong synergic effect | 1:0.06 |
| 1000.0 | 125.0 | 0.927 | 0.339 | Synergic effect | 1:0.13 |
| 2000.0 | 7.8 | 0.710 | 0.592 | Synergic effect | 1:0.0039 |
| 2000.0 | 15.6 | 0.770 | 0.474 | Synergic effect | 1:0.01 |
| 2000.0 | 31.3 | 0.826 | 0.412 | Synergic effect | 1:0.02 |
| 2000.0 | 62.5 | 0.866 | 0.437 | Synergic effect | 1:0.03 |
| 2000.0 | 125.0 | 0.913 | 0.449 | Synergic effect | 1:0.06 |

TABLE 24

<Antitumor agent: doxorubicin, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 41.1523 | 0.389 | 0.356 | Synergic effect | 1:3.00001 |
| 13.7174 | 123.457 | 0.581 | 0.502 | Synergic effect | 1:9.00003 |
| 13.7174 | 370.37 | 0.763 | 0.69 | Synergic effect | 1:27.00001 |
| 41.1523 | 41.1523 | 0.433 | 0.348 | Synergic effect | 1:1 |
| 41.1523 | 123.457 | 0.525 | 0.65 | Synergic effect | 1:3 |
| 123.457 | 41.1523 | 0.408 | 0.534 | Synergic effect | 1:0.33333 |
| 123.457 | 123.457 | 0.537 | 0.719 | Moderate synergic effect | 1:1 |
| 370.37 | 13.7174 | 0.451 | 0.674 | Synergic effect | 1:0.03704 |
| 370.37 | 41.1523 | 0.605 | 0.493 | Synergic effect | 1:0.11111 |
| 370.37 | 123.457 | 0.618 | 0.753 | Moderate synergic effect | 1:0.33333 |
| 1111.11 | 1.52416 | 0.737 | 0.618 | Synergic effect | 1:0.00137 |
| 1111.11 | 4.57247 | 0.706 | 0.713 | Moderate synergic effect | 1:0.00412 |
| 1111.11 | 13.7174 | 0.712 | 0.717 | Moderate synergic effect | 1:0.01235 |
| 1111.11 | 41.1523 | 0.705 | 0.804 | Moderate synergic effect | 1:0.03704 |

TABLE 25

<Antitumor agent: docetaxel, Cancer type: stomach cancer, Cell line: NCI-N87>

| Compound 1 (nM) | Antitumor agent (nM) | Fa | CI | CI_COMMENT | Concomitant ratio |
|---|---|---|---|---|---|
| 100 | 4 | 0.568 | 0.807 | Moderate synergic effect | 1:0.04 |

TABLE 25-continued

<Antitumor agent: docetaxel, Cancer type: stomach cancer, Cell line: NCI-N87>

| Compound 1 (nM) | Antitumor agent (nM) | Fa | CI | CI_COMMENT | Concomitant ratio |
|---|---|---|---|---|---|
| 100 | 8 | 0.707 | 0.716 | Moderate synergic effect | 1:0.08 |
| 200 | 4 | 0.731 | 0.697 | Synergic effect | 1:0.02 |
| 200 | 8 | 0.792 | 0.683 | Synergic effect | 1:0.04 |
| 200 | 16 | 0.848 | 0.709 | Moderate synergic effect | 1:0.08 |
| 400 | 4 | 0.812 | 0.845 | Moderate synergic effect | 1:0.01 |
| 400 | 8 | 0.85 | 0.792 | Moderate synergic effect | 1:0.02 |
| 400 | 16 | 0.879 | 0.816 | Moderate synergic effect | 1:0.04 |

TABLE 26

<Antitumor agent: docetaxel, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 0.457247 | 0.345 | 0.761 | Moderate synergic effect | 1:0.03333 |
| 13.7174 | 1.37174 | 0.691 | 0.21 | Strong synergic effect | 1:0.1 |
| 13.7174 | 4.11523 | 0.791 | 0.257 | Strong synergic effect | 1:0.3 |
| 41.1523 | 1.37174 | 0.71 | 0.206 | Strong synergic effect | 1:0.03333 |
| 41.1523 | 4.11523 | 0.789 | 0.279 | Strong synergic effect | 1:0.1 |
| 123.457 | 1.37174 | 0.651 | 0.407 | Synergic effect | 1:0.01111 |
| 370.37 | 1.37174 | 0.758 | 0.374 | Synergic effect | 1:0.0037 |
| 1111.11 | 0.152416 | 0.787 | 0.679 | Synergic effect | 1:0.00014 |

TABLE 27

<Antitumor agent: docetaxel, Cancer type: non-small cell lung cancer, Cell line: NCI-H226>

| Compound 1 (nM) | Antitumor agent (nM) | Fa | CI | CI_COMMENT | Concomitant ratio |
|---|---|---|---|---|---|
| 500 | 1.25 | 0.640 | 0.265 | Strong synergic effect | 1:0.0025 |
| 500 | 2.50 | 0.723 | 0.195 | Strong synergic effect | 1:0.01 |
| 500 | 5.00 | 0.803 | 0.135 | Strong synergic effect | 1:0.01 |
| 500 | 10.00 | 0.852 | 0.110 | Strong synergic effect | 1:0.02 |
| 500 | 20.00 | 0.855 | 0.157 | Strong synergic effect | 1:0.04 |
| 1000 | 1.25 | 0.538 | 0.771 | Moderate synergic effect | 1:0.0013 |
| 2000 | 1.25 | 0.673 | 0.710 | Moderate synergic effect | 1:0.00063 |

TABLE 28

<Antitumor agent: docetaxel, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 0.457247 | 0.281 | 0.681 | Synergic effect | 1:0.03333 |
| 13.7174 | 1.37174 | 0.618 | 0.129 | Strong synergic effect | 1:0.1 |
| 13.7174 | 4.11523 | 0.766 | 0.097 | Extremely strong synergic effect | 1:0.3 |
| 41.1523 | 0.457247 | 0.281 | 0.705 | Moderate synergic effect | 1:0.01111 |
| 41.1523 | 1.37174 | 0.645 | 0.108 | Strong synergic effect | 1:0.03333 |
| 41.1523 | 4.11523 | 0.751 | 0.116 | Strong synergic effect | 1:0.1 |
| 123.457 | 1.37174 | 0.604 | 0.167 | Strong synergic effect | 1:0.01111 |
| 123.457 | 4.11523 | 0.724 | 0.162 | Strong synergic effect | 1:0.03333 |
| 370.37 | 1.37174 | 0.435 | 0.693 | Synergic effect | 1:0.0037 |
| 370.37 | 4.11523 | 0.589 | 0.56 | Synergic effect | 1:0.01111 |
| 3333.33 | 0.152416 | 0.653 | 0.562 | Synergic effect | 1:0.00005 |
| 3333.33 | 0.457247 | 0.663 | 0.555 | Synergic effect | 1:0.00014 |
| 3333.33 | 1.37174 | 0.672 | 0.584 | Synergic effect | 1:0.00041 |
| 3333.33 | 4.11523 | 0.709 | 0.59 | Synergic effect | 1:0.00123 |

TABLE 29

<Antitumor agent: paclitaxel, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 4.11523 | 0.651 | 0.313 | Synergic effect | 1:0.3 |
| 41.1523 | 4.11523 | 0.625 | 0.38 | Synergic effect | 1:0.1 |
| 123.457 | 4.11523 | 0.615 | 0.454 | Synergic effect | 1:0.03333 |
| 370.37 | 4.11523 | 0.598 | 0.667 | Synergic effect | 1:0.01111 |
| 1111.11 | 0.152416 | 0.601 | 0.777 | Moderate synergic effect | 1:0.00014 |
| 1111.11 | 1.37174 | 0.637 | 0.778 | Moderate synergic effect | 1:0.00123 |
| 1111.11 | 4.11523 | 0.79 | 0.469 | Synergic effect | 1:0.0037 |

TABLE 30

<Antitumor agent: paclitaxel, Cancer type: non-small cell lung cancer, Cell line: NCI-H2170>

| Compound 1 (nM) | Antitumor agent (nM) | Fa | CI | CI_COMMENT | Concomitant ratio |
|---|---|---|---|---|---|
| 100 | 2.00 | 0.574 | 0.669 | Synergic effect | 1:0.02 |
| 100 | 4.00 | 0.746 | 0.528 | Synergic effect | 1:0.04 |
| 100 | 8.00 | 0.821 | 0.579 | Synergic effect | 1:0.08 |
| 200 | 2.00 | 0.753 | 0.576 | Synergic effect | 1:0.01 |
| 200 | 4.00 | 0.832 | 0.507 | Synergic effect | 1:0.02 |
| 200 | 8.00 | 0.891 | 0.475 | Synergic effect | 1:0.04 |
| 400 | 2.00 | 0.871 | 0.590 | Synergic effect | 1:0.01 |
| 400 | 4.00 | 0.892 | 0.577 | Synergic effect | 1:0.01 |
| 400 | 8.00 | 0.912 | 0.593 | Synergic effect | 1:0.02 |

TABLE 31

<Antitumor agent: paclitaxel, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 4.11523 | 0.675 | 0.281 | Strong synergic effect | 1:0.3 |
| 41.1523 | 4.11523 | 0.643 | 0.357 | Synergic effect | 1:0.1 |
| 41.1523 | 12.3457 | 0.777 | 0.367 | Synergic effect | 1:0.3 |
| 123.457 | 4.11523 | 0.636 | 0.386 | Synergic effect | 1:0.03333 |
| 123.457 | 12.3457 | 0.8 | 0.3 | Synergic effect | 1:0.1 |
| 370.37 | 4.11523 | 0.553 | 0.714 | Moderate synergic effect | 1:0.01111 |
| 370.37 | 12.3457 | 0.766 | 0.432 | Synergic effect | 1:0.03333 |

TABLE 32

<Antitumor agent: vemurafenib, Cancer type: malignant melanoma, Cell line: A375>

| Compound 1 (nM) | Antitumor agent (nM) | Fa | CI | CI_COMMENT | Concomitant ratio |
|---|---|---|---|---|---|
| 13.7174 | 123.457 | 0.367 | 0.651 | Synergic effect | 1:9.00003 |
| 13.7174 | 370.37 | 0.494 | 0.768 | Moderate synergic effect | 1:27.00001 |
| 41.1523 | 123.457 | 0.343 | 0.84 | Moderate synergic effect | 1:3 |
| 41.1523 | 370.37 | 0.492 | 0.811 | Moderate synergic effect | 1:8.99998 |

TABLE 33

<Antitumor agent: pemetrexed, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 13.7174 | 123.457 | 0.215 | 0.386 | Synergic effect | 1:9.00003 |
| 13.7174 | 370.37 | 0.436 | 0.238 | Strong synergic effect | 1:27.00001 |
| 13.7174 | 1111.11 | 0.534 | 0.379 | Synergic effect | 1:81.00004 |
| 13.7174 | 3333.33 | 0.623 | 0.643 | Synergic effect | 1:243.00013 |
| 41.1523 | 370.37 | 0.388 | 0.358 | Synergic effect | 1:8.99998 |
| 41.1523 | 1111.11 | 0.526 | 0.424 | Synergic effect | 1:26.99995 |
| 41.1523 | 3333.33 | 0.621 | 0.672 | Synergic effect | 1:80.99985 |
| 123.457 | 1111.11 | 0.484 | 0.633 | Synergic effect | 1:8.99998 |
| 370.37 | 1.52416 | 0.337 | 0.662 | Synergic effect | 1:0.00412 |
| 370.37 | 4.57247 | 0.387 | 0.565 | Synergic effect | 1:0.01235 |
| 370.37 | 13.7174 | 0.278 | 0.835 | Moderate synergic effect | 1:0.03704 |
| 370.37 | 41.1523 | 0.33 | 0.724 | Moderate synergic effect | 1:0.11111 |
| 370.37 | 123.457 | 0.324 | 0.84 | Moderate synergic effect | 1:0.33333 |
| 370.37 | 370.37 | 0.499 | 0.55 | Synergic effect | 1:1 |
| 1111.11 | 1.52416 | 0.726 | 0.578 | Synergic effect | 1:0.00137 |
| 1111.11 | 4.57247 | 0.714 | 0.605 | Synergic effect | 1:0.00412 |
| 1111.11 | 13.7174 | 0.729 | 0.573 | Synergic effect | 1:0.01235 |
| 1111.11 | 41.1523 | 0.745 | 0.541 | Synergic effect | 1:0.03704 |
| 1111.11 | 123.457 | 0.75 | 0.537 | Synergic effect | 1:0.11111 |
| 1111.11 | 370.37 | 0.764 | 0.524 | Synergic effect | 1:0.33333 |
| 1111.11 | 1111.11 | 0.721 | 0.697 | Synergic effect | 1:1 |
| 1111.11 | 3333.33 | 0.749 | 0.79 | Moderate synergic effect | 1:3 |

TABLE 34

<Antitumor agent: pemetrexed, Cancer type: epidermal cancer, Cell line: A431>

| Compound 1 (nM) | Antitumor agent (nM) | Fa | CI | CI_COMMENT | Concomitant ratio |
|---|---|---|---|---|---|
| 13.7174 | 123.457 | 0.554 | 0.273 | Strong synergic effect | 1:9.00003 |
| 13.7174 | 370.37 | 0.638 | 0.38 | Synergic effect | 1:27.00001 |
| 13.7174 | 1111.11 | 0.697 | 0.636 | Synergic effect | 1:81.00004 |
| 41.1523 | 123.457 | 0.509 | 0.409 | Synergic effect | 1:3 |
| 41.1523 | 370.37 | 0.617 | 0.466 | Synergic effect | 1:8.99998 |
| 3333.33 | 1.52416 | 0.536 | 0.551 | Synergic effect | 1:0.00046 |
| 3333.33 | 4.57247 | 0.554 | 0.537 | Synergic effect | 1:0.00137 |
| 3333.33 | 13.7174 | 0.54 | 0.576 | Synergic effect | 1:0.00412 |
| 3333.33 | 41.1523 | 0.534 | 0.657 | Synergic effect | 1:0.01235 |
| 3333.33 | 123.457 | 0.565 | 0.761 | Moderate synergic effect | 1:0.03704 |
| 3333.33 | 370.37 | 0.656 | 0.744 | Moderate synergic effect | 1:0.11111 |

TABLE 35

<Antitumor agent: bortezomib, Cancer type: multiple myeloma, Cell line: RPMI-8226>

| Compound 1 (nM) | Antitumor agent (nM) | Fa | CI | CI_COMMEMT | Concomitant ratio |
|---|---|---|---|---|---|
| 400 | 0.5 | 0.4 | 0.832 | Moderate synergic effect | 1:0.00125 |
| 800 | 0.5 | 0.75 | 0.662 | Synergic effect | 1:0.00063 |

TABLE 35-continued

<Antitumor agent: bortezomib, Cancer type: multiple myeloma, Cell line: RPMI-8226>

| Compound 1 (nM) | Antitumor agent (nM) | Fa | CI | CI_COMMEMT | Concomitant ratio |
|---|---|---|---|---|---|
| 800 | 0.8 | 0.75 | 0.721 | Moderate synergic effect | 1:0.001 |
| 800 | 1 | 0.77 | 0.719 | Moderate synergic effect | 1:0.00125 |

TABLE 36

<Antitumor agent: mitomycin C, Cancer type: large intestine cancer, Cell line: HCT-116>

| Compound 1 (nM) | Antitumor agent (nM) | Fa | CI | CI_COMMENT | Concomitant ratio |
|---|---|---|---|---|---|
| 500.0 | 12.5 | 0.879 | 0.757 | Moderate synergic effect | 1:0.025 |

TABLE 37

<Antitumor agent: lapatinib, Cancer type: stomach cancer, Cell line: NCI-N87>

| Compound 1 (nM) | Antitumor agent (nM) | Fa | CI | CI_COMMENT | Concomitant ratio |
|---|---|---|---|---|---|
| 250 | 3.90625 | 0.728 | 0.658 | Synergic effect | 1:0.016 |
| 250 | 7.8125 | 0.746 | 0.692 | Synergic effect | 1:0.031 |
| 250 | 15.625 | 0.784 | 0.707 | Moderate synergic effect | 1:0.063 |

TABLE 37-continued

<Antitumor agent: lapatinib, Cancer type: stomach cancer, Cell line: NCI-N87>

| Compound 1 (nM) | Antitumor agent (nM) | Fa | CI | CI_COMMENT | Concomitant ratio |
|---|---|---|---|---|---|
| 250 | 31.25 | 0.810 | 0.818 | Moderate synergic effect | 1:0.125 |

TABLE 38

<Antitumor agent: lapatinib, Cancer type: breast cancer, Cell line: UACC-893>

| Compound 1 (nM) | Antitumor agent (nM) | Fa | CI | CI_COMMENT | Concomitant ratio |
|---|---|---|---|---|---|
| 1000 | 62.5 | 0.590 | 0.511 | Synergic effect | 1:0.06 |
| 1000 | 125 | 0.643 | 0.362 | Synergic effect | 1:0.13 |
| 1000 | 250 | 0.629 | 0.613 | Synergic effect | 1:0.25 |
| 1000 | 500 | 0.715 | 0.494 | Synergic effect | 1:0.5 |
| 1000 | 1000 | 0.726 | 0.848 | Moderate synergic effect | 1:1 |
| 2000 | 62.5 | 0.665 | 0.344 | Synergic effect | 1:0.03 |
| 2000 | 125 | 0.710 | 0.246 | Strong synergic effect | 1:0.06 |
| 2000 | 250 | 0.737 | 0.269 | Strong synergic effect | 1:0.13 |
| 2000 | 500 | 0.749 | 0.403 | Synergic effect | 1:0.25 |
| 2000 | 1000 | 0.761 | 0.661 | Synergic effect | 1:0.5 |
| 4000 | 62.5 | 0.708 | 0.333 | Synergic effect | 1:0.02 |
| 4000 | 125 | 0.709 | 0.384 | Synergic effect | 1:0.03 |
| 4000 | 250 | 0.712 | 0.480 | Synergic effect | 1:0.06 |
| 4000 | 500 | 0.746 | 0.488 | Synergic effect | 1:0.13 |
| 4000 | 1000 | 0.783 | 0.576 | Synergic effect | 1:0.25 |
| 8000 | 62.5 | 0.702 | 0.666 | Synergic effect | 1:0.01 |
| 8000 | 125 | 0.722 | 0.542 | Synergic effect | 1:0.02 |
| 8000 | 250 | 0.726 | 0.611 | Synergic effect | 1:0.03 |
| 8000 | 500 | 0.754 | 0.575 | Synergic effect | 1:0.06 |
| 8000 | 1000 | 0.775 | 0.711 | Moderate synergic effect | 1:0.13 |

TABLE 39

<Antitumor agent: lenalidomide, Cancer type: multiple myeloma, Cell line: MM.1S>

| Compound 1 (nM) | Antitumor agent (nM) | Fa | CI | CI_COMMENT | Concomitant ratio |
|---|---|---|---|---|---|
| 13.7174 | 15.2416 | 0.227 | 0.657 | Synergic effect | 1:1.11111 |
| 13.7174 | 45.7247 | 0.323 | 0.551 | Synergic effect | 1:3.33334 |
| 13.7174 | 137.174 | 0.493 | 0.284 | Strong synergic effect | 1:10 |
| 13.7174 | 411.523 | 0.618 | 0.225 | Strong synergic effect | 1:30.00007 |
| 13.7174 | 1234.57 | 0.735 | 0.168 | Strong synergic effect | 1:90.00029 |
| 13.7174 | 3703.7 | 0.765 | 0.293 | Strong synergic effect | 1:270.00015 |
| 13.7174 | 11111.1 | 0.776 | 0.693 | Synergic effect | 1:810.00044 |
| 41.1523 | 15.2416 | 0.244 | 0.806 | Moderate synergic effect | 1:0.37037 |
| 41.1523 | 45.7247 | 0.376 | 0.523 | Synergic effect | 1:1.11111 |
| 41.1523 | 137.174 | 0.536 | 0.329 | Synergic effect | 1:3.33333 |
| 41.1523 | 411.523 | 0.652 | 0.263 | Strong synergic effect | 1:10 |
| 41.1523 | 1234.57 | 0.756 | 0.206 | Strong synergic effect | 1:30.00002 |
| 41.1523 | 3703.7 | 0.777 | 0.317 | Synergic effect | 1:89.99983 |
| 123.457 | 137.174 | 0.552 | 0.67 | Synergic effect | 1:1.11111 |

TABLE 39-continued

<Antitumor agent: lenalidomide, Cancer type: multiple myeloma, Cell line: MM.1S>

| Compound 1 (nM) | Antitumor agent (nM) | Fa | CI | CI_COMMENT | Concomitant ratio |
|---|---|---|---|---|---|
| 123.457 | 411.523 | 0.693 | 0.463 | Synergic effect | 1:3.33333 |
| 123.457 | 1234.57 | 0.788 | 0.352 | Synergic effect | 1:10 |

Incidentally, gemcitabine exhibited the same synergic effect as in NCI-H522 even in other non-small cell lung cancers (NCI-H441, NCI-H520). Cisplatin exhibited the same synergic effect as in A549 even in other non-small cell lung cancers (NCI-H2170, NCI-H226, NCI-H441, NCI-H520, NCI-H522, PC-14). Doxorubicin exhibited the same synergic effect as in SBC-1 even in other small cell lung cancers (NCI-N417). Docetaxel exhibited the same synergic effect as in NCI-H226 even in other non-small cell lung cancers (NCI-H2170). Paclitaxel exhibited the same synergic effect as in NCI-H2170 even in other non-small cell lung cancers (HCC827, NCI-H1975). Lapatinib exhibited the same synergic effect as in UACC-893 even in other breast cancers (BT-474, JIMT-1, MDA-MB-361, MDA-MB-453, SK-BR-3, UACC-812).

As described above, it was clearly found that the azabicyclo compound of the invention or a salt thereof exhibited a strong synergic effect with extremely various ranges of antitumor agents having different action mechanisms.

The invention claimed is:

1. A method for treating a tumor, comprising:
   administering to a patient 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof and at least one antitumor agent selected from the group consisting of mitomycin C, 5-fluorouracil, bortezomib, vemurafenib, and 5-(4-bromo-2-chlorophenylamino)-4-fluoro-1-methyl-1H-benzimidazole-6-carbohydroxamic acid 2-hydroxyethyl ester (ZD6244)",
   wherein the patient's tumor is selected from the group consisting of colorectal cancer, colon cancer, rectal cancer, malignant melanoma, epidermal cancer, and multiple myeloma.

2. The method of claim 1, wherein the antitumor agent and the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof are administered to the patient simultaneously or separately.

3. The method of claim 1, wherein the salt of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide is at least one selected from the group consisting of an acid addition salt of an inorganic acid, an acid additional salt of an organic acid, a salt of an inorganic base, a salt of an organic base, a salt of a basic amino acid, and an ammonium salt.

4. The method of claim 1, wherein a molar ratio of the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof to the antitumor agent is from 1:0.00014 to 3645.

5. The method of claim 1, wherein a molar ratio of the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof to the antitumor agent is from 1:0.00014 to 0.3.

6. The method of claim 1, wherein the antitumor agent is administered to the patient prior to administering the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof to the patient.

7. The method of claim 1, wherein the antitumor agent and the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof are administered to the patient simultaneously.

8. The method of claim 1, wherein the antitumor agent and the 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide or a salt thereof are administered to the patient separately.

9. The method of claim 6, wherein the salt of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide is at least one selected from the group consisting of an acid addition salt of an inorganic acid, an acid additional salt of an organic acid, a salt of an inorganic base, a salt of an organic base, a salt of a basic amino acid, and an ammonium salt.

10. The method of claim 7, wherein the salt of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide is at least one selected from the group consisting of an acid addition salt of an inorganic acid, an acid additional salt of an organic acid, a salt of an inorganic base, a salt of an organic base, a salt of a basic amino acid, and an ammonium salt.

11. The method of claim 8, wherein the salt of 3-ethyl-4-{3-isopropyl-4(4-(1-methyl-1H-pyrazol-4-yl)-1H-imidazol-1-yl)-1H-pyrazolo[3,4-b]pyridin-1-yl}benzamide is at least one selected from the group consisting of an acid addition salt of an inorganic acid, an acid additional salt of an organic acid, a salt of an inorganic base, a salt of an organic base, a salt of a basic amino acid, and an ammonium salt.

* * * * *